US008935753B1

(12) United States Patent
Cha et al.

(10) Patent No.: US 8,935,753 B1
(45) Date of Patent: Jan. 13, 2015

(54) NETWORK BASED HEALTHCARE MANAGEMENT SYSTEM

(75) Inventors: Hyuk Cha, Glenelg, MD (US); James Birger, Sykesville, MD (US); Alexandra N. Cha, Glenelg, MD (US)

(73) Assignee: Healthcare Interactive, Inc., Glenwood, MD (US)

( * ) Notice: Subject to any disclaimer, the term of this patent is extended or adjusted under 35 U.S.C. 154(b) by 787 days.

(21) Appl. No.: 12/484,887

(22) Filed: Jun. 15, 2009

Related U.S. Application Data

(63) Continuation-in-part of application No. 12/391,223, filed on Feb. 23, 2009.

(60) Provisional application No. 61/030,721, filed on Feb. 22, 2008, provisional application No. 61/061,318, filed on Jun. 13, 2008, provisional application No. 61/129,356, filed on Jun. 20, 2008, provisional application No. 61/073,926, filed on Jun. 19, 2008.

(51) Int. Cl.
*G06F 15/16* (2006.01)

(52) U.S. Cl.
USPC .................. 726/4; 726/26; 726/27; 709/207

(58) Field of Classification Search
CPC ..... H04L 63/101; H04L 63/08; H04L 63/102; H04L 29/06829; H04L 29/0685
USPC .................. 726/4, 26, 27; 709/207
See application file for complete search history.

(56) References Cited

U.S. PATENT DOCUMENTS

| 5,414,852 | A  | * | 5/1995  | Kramer et al. ............... 718/104 |
|-----------|----|---|---------|--------------------------------------|
| 5,842,173 | A  |   | 11/1998 | Strum et al.                         |
| 5,995,937 | A  |   | 11/1999 | DeBusk et al.                        |
| 2002/0035638 | A1 | * | 3/2002 | Gendron et al. ............... 709/238 |
| 2002/0178119 | A1 | * | 11/2002 | Griffin et al. ................... 705/54 |
| 2003/0009355 | A1 |   | 1/2003  | Gupta                                |
| 2003/0050794 | A1 |   | 3/2003  | Keck                                 |
| 2005/0050152 | A1 | * | 3/2005 | Penner et al. ................. 709/207 |
| 2005/0182661 | A1 | * | 8/2005 | Allard et al. ...................... 705/3 |
| 2005/0222867 | A1 |   | 10/2005 | Underwood et al.                    |
| 2006/0109961 | A1 |   | 5/2006  | Mahesh et al.                        |
| 2007/0168461 | A1 |   | 7/2007  | Moore                                |
| 2007/0198296 | A1 |   | 8/2007  | Pellinat et al.                      |

(Continued)

OTHER PUBLICATIONS

Wilikens et al, A context-related authorization and access control method based on RBAC: 7/02/0006; ACM 1-58113-496; pp. 117-124.*
Shengli Wu et al., Authorization and Access Control of Application Data in Workflow SystemsJournal of Intelligent Information System 18, 71-94, Kluwer Academic Publishers. Manufactured in The Netherlands, 2002.*

(Continued)

*Primary Examiner* — Harunur Rashid
(74) *Attorney, Agent, or Firm* — Rosenberg, Klein & Lee

(57) ABSTRACT

A network based healthcare management system is provided. The system includes a plurality of client workstations and a plurality of healthspace service processors. The healthspace service processors access at least one database remotely disposed relative to the client workstations with the healthspace service processors providing access to predetermined healthspace resources. The system further includes a healthspace service interface unit operably coupled to the client workstations and healthspace service processors to selectively actuate at least one of the healthspace service processors responsive to the client workstations. The healthspace service interface unit including an efficiency module which adaptively maintains a plurality of parametric indicia with respect to optimum healthspace resource utilization.

14 Claims, 27 Drawing Sheets

(56) References Cited

U.S. PATENT DOCUMENTS

| | | |
|---|---|---|
| 2007/0255584 A1 | 11/2007 | Pavlatos et al. |
| 2007/0294302 A1* | 12/2007 | Besch et al. ............... 707/104.1 |
| 2008/0005054 A1 | 1/2008 | Kurian et al. |
| 2008/0027753 A1 | 1/2008 | Dean |
| 2008/0082363 A1 | 4/2008 | Habashi |
| 2009/0099562 A1 | 4/2009 | Ingimudarson et al. |
| 2009/0177641 A1* | 7/2009 | Raghavan ......................... 707/5 |
| 2010/0077487 A1* | 3/2010 | Travis et al. .................... 726/28 |

OTHER PUBLICATIONS

Bacon et al., A Model of OASIS Role-Based Access Control and Its Support for Active Security, ACM Transactions on Information and System Security, vol. 5, No. 4, Nov. 2002, pp. 492-540.*

Kulkarni et al., Context-Aware Role-based Access Control in Pervasive, SACMAT'08, Jun. 11-13, 2008, Estes Park, Colorado, USA. Copyright 2008 ACM 978-1-60558-129-3/08/06, pp. 113-122.*

* cited by examiner

| Company Reports (Secure) | | | | | | | |
|---|---|---|---|---|---|---|---|
| Select Company Report: | CompanyRiskProfile ▽ | | | | | | |
| | CompanyRiskProfile | | | | | | |
| ☐ ◁ 1 of 1 | CompanyRiskSummary | | | ▽ | | Find | Next |
| Risk Profile & Poten | SMR Report | | | | | | |

| | Conditions Categories | Total# Conditions | High Risk Conditions | High Risk Potential Cost | Medium Risk Conditions | Medium Risk Potential Cost | Low Risk Conditions | Low Risk Potential Cost | Average Annual Cost |
|---|---|---|---|---|---|---|---|---|---|
| ⊟ | Allergy/Immunology | 61 | 4 | $49,516 | 20 | $247,580 | 37 | $458,023 | $12,379 |
| | Cardiovascular | 92 | 11 | $184,151 | 53 | $887,273 | 28 | $468,748 | $16,741 |
| | Cardiovascular / Chronic Medical | 6 | 0 | $0 | 6 | $100,446 | 0 | $0 | |
| | Cardiovascular / Congestive Heart Failure | 2 | 1 | $16,741 | 1 | $16,741 | 0 | $0 | |
| | Cardiovascular / High Blood Pressure | 52 | 6 | $100,446 | 28 | $468,748 | 18 | $301,338 | |
| | Cardiovascular / Hyperlipidemia | 27 | 3 | $50,223 | 14 | $234,374 | 10 | $167,410 | |
| | Cardiovascular / Vascular Disorders | 5 | 1 | $16,741 | 4 | $66,964 | 0 | $0 | |
| ⊞ | Ear, Nose, Throat (ENT) | 7 | 0 | $0 | 2 | $18,078 | 5 | $45,195 | $9,039 |
| ⊞ | Endocrine | 48 | 8 | $80,496 | 28 | $281,736 | 12 | $120,744 | $10,062 |
| ⊞ | Eye | 27 | 0 | $0 | 4 | $42,896 | 23 | $246,652 | $10,724 |
| ⊞ | Female Reproductive | 57 | 0 | $0 | 16 | $196,800 | 41 | $504,300 | $12,300 |
| ⊞ | Gastrointestinal/Hepatic | 43 | 6 | $76,464 | 28 | $386,832 | 9 | $114,696 | $12,744 |
| ⊞ | Genitourinary | 10 | 0 | $0 | 9 | $110,700 | 1 | $12,300 | $12,300 |
| ⊞ | Infectious Disease | 104 | 3 | $48,174 | 36 | $578,088 | 65 | $1,043,770 | $16,058 |
| ⊞ | Malignancies/Cancer | 4 | 2 | $38,550 | 2 | $38,550 | 0 | $0 | $19,275 |
| ⊞ | Musculoskeletal | 4 | 1 | $22,243 | 3 | $66,729 | 0 | $0 | $22,243 |
| ⊞ | Neurological | 13 | 1 | $13,942 | 10 | $139,420 | 2 | $27,884 | $13,942 |
| ⊞ | Psychosocial | 57 | 5 | $41,375 | 37 | $306,175 | 15 | $124,125 | $8,275 |
| ⊞ | Respiratory System | 67 | 2 | $24,758 | 17 | $210,443 | 48 | $594,192 | $12,379 |
| ⊞ | Skin (Integumentary) | 81 | 4 | $41,632 | 14 | $145,712 | 33 | $343,464 | $10,408 |
| | Totals | 645 | 47 | $621,301 | 279 | $3,627,012 | 319 | $4,104,093 | |

NETWORK BASED HEALTHCARE MANAGEMENT SYSTEM

RELATED APPLICATIONS

This is a Continuation In Part Application based on U.S. Non-Provisional application Ser. No. 12/391,223, filed 23 Feb. 2009, which is based on U.S. Provisional Application Nos. 61/030,721, filed 22 Feb. 2008; 61/061,318, filed 13 Jun. 2008; 61/129,356, filed 20 Jun. 2008; and 61/073,926, filed 19 Jun. 2008.

BACKGROUND OF THE INVENTION

The present invention is generally directed to a healthcare management system. The healthcare management system includes a framework of databases, proxies, services, processors, a front end Healthspace service Application Programming Interface (API) or Healthspace framework (used interchangeably herein) using a web service and internet gateway to interconnect heterogeneous clients. The system not only interconnects various service providers and clients but also provides methodologies for measuring efficiency and providing incentives, suggestions, and means to improve the performance and efficient utilization of healthcare services by consumers and service providers. Still further, the system provides for relationship based security and methods for increasing effectiveness of communicating healthcare information.

The U.S. healthcare system is the most costly in the world. Healthcare is out of control in America. There are many providers of healthcare who each medications, billing, and claims. Every person has a detailed medical history that could be relevant to future diagnoses and to the treatment of potential problems, yet all of the various practitioners are separate and maintain different records that are proprietary, incompatible, unconnected and generally inaccessible. Health costs are rising and a large portion of this is due to inefficient use of healthcare. Some inefficiencies include the disconnected nature of practitioners and clients, the lack of cooperation between practitioners, the inappropriate use of brand named drugs as opposed to generic drugs, a general apathy on the part of the client and also, in large part, due to lack of accurate information presented to clients or patients. Of the information that is out there and that is indeed broadcast accurately to relevant patients, there is a tendency for these people to just ignore or not be motivated to change their behaviors to increase their health or efficient user of their healthcare benefits. People are inundated with so much junk mail and spam, solicitations, and advertisements that the only way to cope is to block out a large portion of this as noise and unwanted and throw it away or ignore it.

So there exists a need to interconnect all of the different medical practitioners with billing and insurance adjustment, prescription providers, the end-user, client, patient, or consumer, and also to inform them of better practices and effectively communicate with them to motivate them to change behavior to be more healthful and efficient in use of funds, medicines, and benefits. Still further, there exists a need to ensure access to records is constrained solely to authorized entities.

SUMMARY OF THE INVENTION

It is an object of the present invention to provide a system and method which provides a framework for practitioners and service providers to serialize, standardize, and provide medical information to authorized consumers and service providers.

It is another object of the present invention to provide a system and method which restricts access to medical records to only the owner of the records and those granted an explicit or inherited relationship of trust with the owner.

It is a further object of the present invention to provide a system and method for interlinking clients or patients with care providers and service providers to facilitate communications, scheduling, and coordination.

It is still another object of the present invention to provide a system and method for monitoring the efficiency of users and comparing them based on benchmarks and by comparisons to their peer groups.

Yet another object of the present invention is to provide a system and method for analyzing how users and service providers increase their efficiency index within the system and communicating this to other users to enable them to similarly increase their efficiency index as well.

It is a further object of the present invention to provide a system and method which segments users to enable one to more successfully motivate and encourage these groups of users to change behaviors or increase their efficient use of healthcare options and benefits.

Another object of the present invention is to provide a system and method which analyzes and optimizes messaging to users to effectuate a change.

These and other objects are attained in a system and method formed in accordance with the present invention for a network based healthcare management system. In an embodiment of the system and method, a healthcare management system is programmably implemented in at least one server apparatus. The server apparatus may be any type of server apparatus known in the art. The server apparatus maintains a plurality of databases of different information, for example physician management, customer service, patient management, communications, prescriptions. Some databases of the system are not maintained in-house, but instead, are brought in as proxies, for example: Aetna Claims Management Database residing on an Aetna server may be proxied in and treated as a virtual database, or a CVS prescription database maintained on the CVS server may be proxied in and treated as a virtual database on the current system. Any known type of database structure may be used.

The information on the databases is retrieved using services either: residing on the external servers of care providers, or on services residing within an in-house server. Rather than provide the end-users, clients, patients, individuals, or consumers (used interchangeably herein) with direct access to the services, a Healthspace service application programming interface (API) is provided with modules such as: client and service registration, service operator (which operates as a marshal), security model, healthcare efficiency index, and Healthspace economy. A Healthspace client or end-user may access the system on their choice of platform, be it a workstation, phone, or PDA through an internet gateway/web service gateway. Additionally, other service providers may also interface with the Healthspace service through their workstations or servers accessing the Healthspace service through the internet gateway/web service gateway.

BRIEF DESCRIPTION OF THE DRAWINGS

FIG. 22 is an illustrative example of a display of predictive model of a graphical user interface of a second application of an exemplary embodiment of the present invention;

FIG. 24 is an illustrative example of a display of a graphical user interface of an application of an exemplary embodiment of the present invention;

DESCRIPTION OF THE PREFERRED EMBODIMENTS

Figure 1:
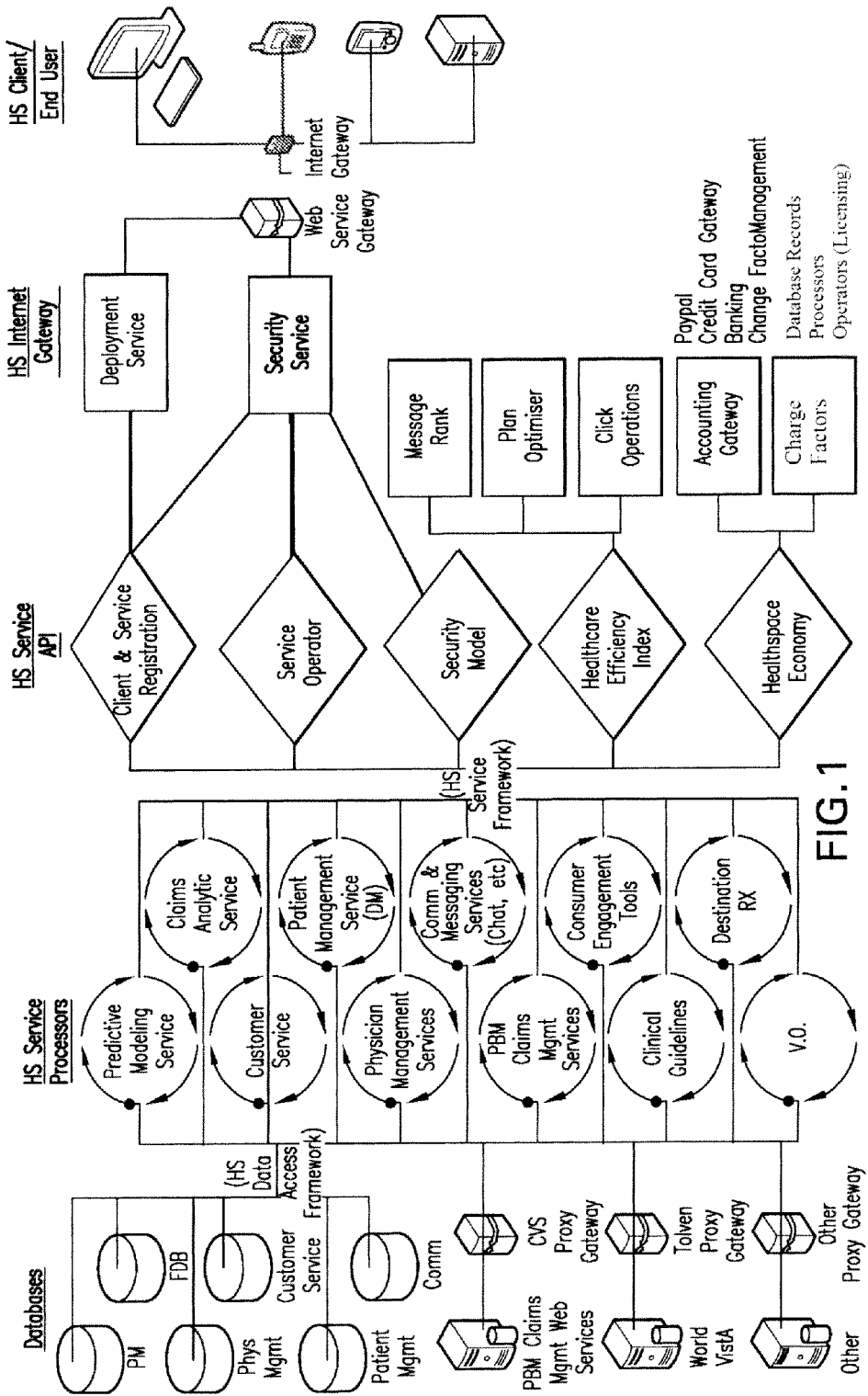
FIG. 1 is a schematic block diagram illustrating an exemplary arrangement of nodes of a system architecture within a portion of a hierarchical tree defined in accordance with the present invention.
Figure 2:
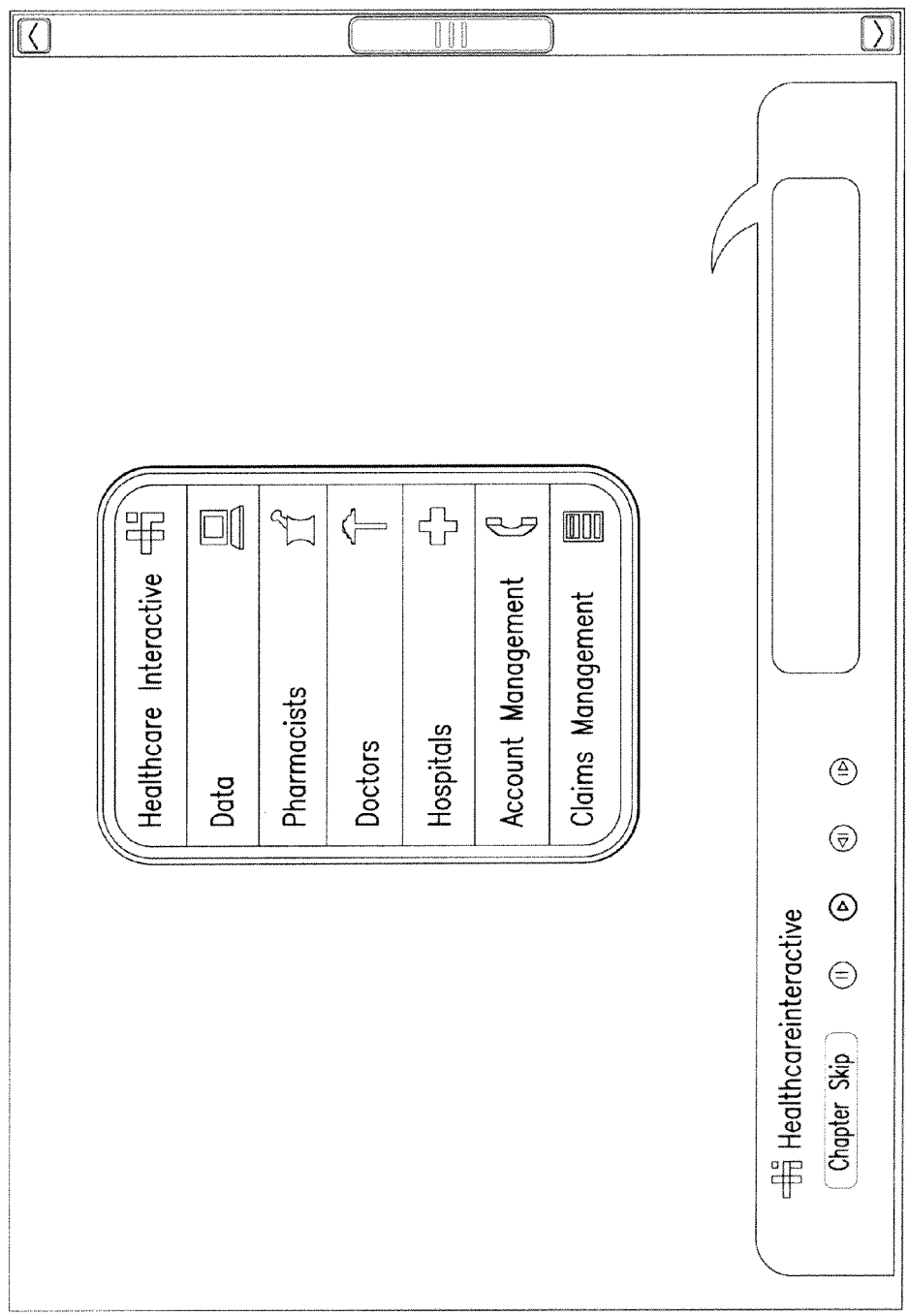
FIG. 2 is an illustrative example of a display of a graphical user interface of an application of an exemplary embodiment of the present invention.

A network based healthcare management system according to the present invention includes a framework (Healthspace framework) based preferably on a service oriented architecture (SOA) designed to support differing types of applications. As seen in FIG. 1, the framework provides a plurality of different services, each generally performing an atomic, or discrete, function. A subset of the universe of services is chosen for each specific application. In one embodiment, the application is a healthcare management application, and includes, illustratively, services such as: predictive modeling, claims analytic service, customer service, patient management service, physician management services, communications and messaging services, claims management services, consumer engagement tools, clinical guidelines, and prescription drugs.

Each of the services accesses at least one database that it draws information from and potentially saves information to. Illustratively, these databases include a database of physicians, a database of customer service, patient management database, communications database, prescriptions database, or the like. These databases, collectively called a dataspace, may be maintained on-site on the server, or they may be accessed through a proxy gateway which will treat a database located on an external service provider's server as if it were a local database contained within the Healthspace framework itself. In this manner, the various services that the Healthspace framework provides are able to tie in a heterogeneous mix of different service providers, practitioners, caretakers, and caregivers and the various services may access and serialize their independent, proprietary database formats irrespective of the proprietary formatting and treat the proprietarily formatted data as if it was in a uniform format thereby making it easily accessible through a consolidated, universal network such as the healthcare network of the instant invention. Furthermore, queries are able to be made uniform across these disparate database sources. Not only are the databases able to be located on external service providers servers, but also the framework is able to utilize services that are provided by the external service providers. For example, the framework is able to utilize services residing and provided by an insurance provider or a pharmacy or a doctor's office and those services are incorporated and used seamlessly by the framework of the instant invention.

The framework itself, which may be thought of as the glue that pulls all the disparate services in the Healthspace together, moderating client features and service operations, may be implemented in Microsoft .Net version 3.5, using Windows Communication Foundation (WCF) with a C# (C sharp) language. The framework may utilize Language Integrated Query (LINQ), LINQ-to-Structured Query Language (SQL) and LINQ-to-Extensible Markup Language (XML) to facilitate access to necessary data. Thereby, universal query language may be used to support multiple database types including relational, DB2, and Oracle, et cetera. Windows Presentation Foundation (WPF) may be used to build client applications that will interact with the framework.

The framework comprises several assemblies or code libraries, including, illustratively:

An Hciactive.Healthspace assembly which serves as the main framework assembly. The Hciactive.Healthspace assembly contains utilities and classes used by both clients and server applications in the framework. A set of custom exceptions and exception handling mechanisms are defined to react in certain defined ways to special conditions which change the normal flow of execution. In the event that a supported exception is generated and thrown or reported by a server, it may be converted to a WCF fault to match the IHealthspace fault contracts. There are four general varieties of faults, including: UserInputErrorFaul, SecurityFault, ConfigurationFaul, and a general ServiceFault.

The Hciactive.Healthspace.Services.Database assembly which may include, among other functions, basic database functions, extension methods, and transaction capabilities.

The Hciactive.Healthspace.Services assembly contains the classes needed to register and control client and service operations.

The Hciactive.Healthspace.Services.Host assembly contains the classes that implement the actual WCF host.

The Hciactive.Healthspace.Services.Security assembly contains classes to control authorization of client features and service operations.

The Hciactive.Healthspace.Client assembly contains classes to expose and provide selected features to a client application.

This dynamic framework allows addition of new services, deletion of outdated services, or modification of existing services. To keep track of available services, the framework provides for service registration. Each service is associated with a class that implements the service. Within a service, there may be one or more service operations. The service operations provide entry points to individual transactions or procedures that a service may perform.

Similarly, clients are registered as well. Client registration involves specifying which clients will use the Healthspace framework and what they are allowed to do in the Healthspace framework. Clients are segmented into Client Features; the Client Features are then able to be activated or deactivated based on individual user security, roles, and preferences. Client features are registered with the service operations that they may call such that the security system may properly allow granular access. A client seeking to access a service operation that has not been registered will receive an access denied exception. If no service operations are registered with a client's features, then there are no calls that the client may make without getting access denied exceptions.

Security is based on a combination of both client application features and user privileges. A user may have access to an operation, but the client application may not. For example, a doctor working with a chat program likely has rights to modify a patient's medical records, but the chat program is not designed to do so and does not provide the necessary features. Conversely, a client may be designed to use an operation that the user working with the client does not have privilege to access. As another example, a customer service representative may be logged into a medical records system that has the facility to modify patient records, but the user specifically does not have that right. Therefore, based on client feature registration, and individual user roles, the gateway would restrict access to the service to modify patient records in the two aforementioned situations. On each service operation call, a session token (identifying the user, the client application, and an expiration) should be provided. The framework will check for appropriate permissions before enabling the client to call an operation.

The framework provides a mechanism for calling the many constituent services in a unified and standard manner. Service operations are referenced by name. The service name and the operation name together identify a unique function from the complete list of operations across all services. To allow for flexibility, each service operation is preferably called with a single XML input parameter and returns a single XML output. The single XML input and outputs may be complex data structures containing many values serialized in XML format.

To ensure security and restricted access to files, services, and information, different levels of security, authentication, and certification are employed. For example, end-users and clients, or consumers, are not able to directly access the services or databases that are provided, and instead are insulated through several layers including the Healthspace API, the internet gateway, and the Healthspace client software residing on the end-user's device.

The end-user's device, whether it be a home computer, PDA, cell phone, kiosk, or even a set top box, will have individually written client software which has defined system calls and a user interface defined, for instance, through eXtensible Application Markup Language (XAML) or WPF which defines the limited manner in which the end-user may interface with the client and the Healthspace service API and, ultimately, the services and databases. Deployment services are supplied as an added feature of Healthspace. Client assemblies may be packaged for execution on target environments for one click or (ClickOnce) deployment.

A first layer to preventing unauthorized use is to secure use of the client program by a user name and password, biometrics, or another secure mechanism known to one of skill in the art. After a user has entered a user name and password, or otherwise authenticated himself or herself, the client program authenticates not only the end-user, but also, the client program itself to a remote server by any suitable means known in the art. This may include use of a certificate or checksums or any other such measures. The goal of this is to ensure that the client is an authenticated and certified client program, and not a home-brew client program or a malicious type of unauthorized software, such as a bot. In this manner the healthcare management system is able to regulate the initial system calls coming from the end-user.

Once the healthcare management system client program and the end-user have been authenticated as being an authorized user and client program of the system, the security service of the Healthspace service API provides access to managed features (rights to do something) to an end-user and that client program. Essentially, this allows a specific client program and a specific end-user to perform a certain subset of all tasks. This is generally role based. For example, a consumer, or end-user, is not permitted to prescribe their own medication. Only a physician is permitted to prescribe medication to one of their patients. As another example, not just any physician is permitted to add a health reminder. Instead, only a physician that has a confirmed relationship with the end-user, or patient, associated with the user name and password is permitted to do so.

Still further, there is a bifurcation of the ability to access managed features (rights to do something) versus access of private data (permissions to see something). Access to managed features is preferably role based. For example, a physician may add a healthcare reminder. With the access of private data (permission to see something), access may alternatively be identity based. For example, an end-user associated with a specific user name and password is able to see their own healthcare data, and in certain circumstances, his/her spouse's healthcare data.

Client-Server communication may preferably be implemented in XML. The framework provides functionality through Web Services (using WCF). The Healthspace framework may generally follow an exemplary message loop including:

(1) A Client application initiates a session with a server using the Healthspace web service call including a logon of client id, username, and password to create a session token. The client id may be an identifier of the specific revision or version number of the client application software, or may denote a type of client software e.g. consumer vs. provider vs. administrator.

(2) The client associated with the created session token retrieves an access control list and a client configuration selected to be relevant to the user initiating the session by using the web service to call functions: GetClientFeatureAccess and GetClientFeatureConfig.

(3) The client application displays "client features" to the user based on the user's access (defined by the access control list), preferences, what the application supports, and the client configuration.

(4) For the Client to communicate with a server, the client repeatedly executes "service operations." The service operations are executed through a web service call: Execute(sessionId, serviceOperationId, XmlParameters). The session id, service operation id, and XML parameters are provided to the call with XML results being returned.

Service operations provide a mechanism for calling the many constituent services in a unified and standard way. Service operations are single stateless method calls with the standardized method signature: public delegate XElement ServiceOperationName (XElement parameters). Service operations are registered with Healthspace to be executed by services running in the context of the server host. Based on the session context, the server determines if the client/user combination may call the server feature being requested. If, based on the session context, the client/user combination is unable to call the server feature being requested, an AccessDenied fault may be generated.

(5) The session is ended with a Logoff.

Member services are shared by all services with the session being stored in a database. The Hciactive.Healthspace.Client assembly provides user authentication, member and session management services. The main class in the assembly is the Session class. Through this class, a client application may log on and log off users. The Session class may also invoke server features through a web service. The main methods of this Session class include: Logon, Logoff, Execute, ExecuteFileTransfer, and GetDataPage.

Additional security is maintained through only providing a few entry points into the framework including:

Logon: Begins a session with the user and a particular client. The client is given a session token which is used with other calls to identify the user and client combination.

ChangePassword;

Logoff: Ends a session with a user and particular client, forcing expiration of the session token;

Execute: Allows a client to interact with services using XML messaging;

ExecuteFileTransfer: Allows a client to interact with services to pass raw binary messaging;

GetClientFeatureAccess: Provides a list of the client features that a user is permitted to use in a session. This is used to enable the client to selectively hide/show elements of the user interface based on their access level.

GetClientFeatureConfiguration: Returns to the client an XML configuration file for a specific client feature. This may be used to allow dynamic form building as well as allowing the user to save preferences.

The Hciactive.Healthspace.Services.Security assembly provides tools to authorize users. This assembly is used by the client applications to grant or decline permissions to certain users based on roles.

A client application may execute remote server functionality through service operations. The service operations are hosted in the server application and are invoked by the client through the Hciactive.Healthspace.Client.Session class (using the aforementioned Execute, ExecuteFileTransfer, or the GetDataPage methods).

To create a service operation, the Hciactive.Healthspace.Services.Iservice interface is implemented. The methods to be exposed should be marked or flagged with the [ServiceOperation] attribute which is preferably contained in HciActive.Healthspace.Services.ServiceOperationAttribute. In order to expose a method as a service feature, it should comply with a signature such as:

[ServiceOperation]
public XElement ServiceFeatureName (XElement parameters)

Such a signature indicates that a particular method may be used as a service feature. As the method signature uses XElement parameters, service features should use LINQ-to-XML XElement objects to receive the XElement input parameters and return values.

For each Execute call of a service operation, the server performs several steps, including:

(1) verifying authorization;
(2) determining the service responsible for the server feature;
(3) creating an instance of the service class through Reflection;
(4) calling configure on the service class;
(5) setting the CurrentSessionContext object (having sessionId, clientId, and principalId);
(6) executing the service method responsible for the ServerFeature;
(7) disposing of the service.

Each service operation should be developed in a "stateless" way. If information or context needs to be preserved between two or more separate Execute calls, the information or context should be stored in a database. Generally, the information or context to be saved between separate Execute calls should not be written in such a way that a first service operation starts an operation, and a second service operation finishes that same operation. Preferably, a single service operation completes the entirety of an operation. Alternatively, an operation may be broken down into multiple states that may be stopped and reconstructed at will. In this alternative embodiment, each of the multiple states should have their own service operation.

A client application may define several client features. A client feature means that the client is declaring that it is going to use a service operation. Client features use Access Control Lists (ACL) to allow or deny access to client features to the specified user. The Healthspace framework has mechanisms to allow a given client application to show or hide graphical elements depending on an ACL.

The web project that publishes WCF services should have the following exemplary configuration in order to register service operations to the framework:

```
<hciactive.healthspace.services.host SecurityService="Security">
    <glebalSettings>
    </globalSettings>
    <services>
        <service name="Security"
serviceType="Hciactive.Healthspace.Services.SecurityService"
assembly="bin\Hciactive.Healthspace.Services.Security.dll">
            <settings>
                <add name=connection" value="Healthspace"/>
            </settings>
        </service>
        <service name="P2PHC.IM"
serviceType="P2PHC.Services.IMServices"
assembly="bin\P2PHC.Services.dll">
            <settings>
                <add name="connection" value="Healthspace"/>
            </settings>
        </service>
        <service name="P2PHC.Cal"
serviceType="P2PHC.Services.CalendarServices"
assembly="bin\P2PHC.Services,dll">
            <settings>
                <add name="connection" value="Healthspace"/>
            </settings>
        </service>
    </services>
    <clients>
        <client clientId="P2PHC.Client">
            <clientFeature name="P2PHC.Client.IMClientFeature">
                <serviceOperation
                operationId="P2PHC.IM.GetContactList"/>
                <serviceOperation
                operationId="P2PHC.IM.SendMessage"/>
                <serviceOperation
operationId="P2PHC.IM.GetNotificationList"/>
            </clientFeature >
            <clientFeature name="P2PHC.Client. CalendarClientFeature ">
                <serviceOperation
operationId="P2PHC.Cal.DeleteAppointment"/>
                <serviceOperation
operationId="P2PHC.Cal.SaveAppointment"/>
                <serviceOperation
operationId="P2PHC.Cal.GetAppointmentList "/>
            </clientFeature>
        </client>
    </clients>
</hciactive.healthspace.services.host>
<appSettings/>
<connectionStrings>
    <add name="Healthspace" connectionString="Data
Source=(local);Initial Catalog=Healthspace;Integrated Security-True"
/>
</connectionStrings>
```

Client applications should define a WCF endpoint in an App.config file like the following exemplary code, where the server name specified in the Uniform Resource Locator (URL) should be where the WCF project is running (where the service operations reside):

```
<system.serviceModel>
    <bindings>
        <wsHttpBinding>
            <binding name="WSHttpBinding_IHealthspace"
closeTimeout="00:01:00"
                openTimeout="00:01:00"
                receiveTimeout="00:10:00"
                sendTimeout="00:01:00"
                bypassProxyOnLocal="false"
                transactionFlow="false"
                hostNameComparisonMode="StrongWildcard"
                maxBufferPoolSize="524288"
            maxReceivedMessageSize="65536"
                messageEncoding="Text" textEncoding="utf-8"
                useDefaultWebProxy="true"
                allowCookies="false">
                <readerQuotas maxDepth="32"
                    maxStringContentLength="8192"
                        maxArrayLength="16384"
                        maxBytesPerRead="4096"
                        maxNameTableCharCount="16384" />
                    <reliableSession ordered="true"
                inactivityTimeout="00:10:00"
                        enabled="false" />
                    <security mode="Message">
                        <transport
        clientCredentialType="Windows"
                            proxyCredentialType="None"
    realm=" " />
                        <message clientCredentialType="Windows"
                            negotiateServiceCredential="true"
                            algorithmSuite="Default"
                            establishSecurityContext="true" />
                    </security>
            </binding>
        </wsHttpBinding>
    </bindings>
    <client>
        <endpoint
        address="http://ServerName/P2PHC.Web/Healthspace.svc"
            binding="wsHttpBinding"
            bindingConfiguration="WSHttpHinding_IHealthspace"
            contract="HealthspaceServicesReference.IHealthspace"
            name="WSHttpHinding_IHealthspace">
        </endpoint>
    </client>
</system.serviceModel>
```

While the invention of the subject Patent Application provides for very fine-grained setting of access controls, it may not be effective in all applications to individually set and unset each specific permission for each end-user based on each service provider. Preferably, default profiles of relationships are established.

For example, when an end-user or a patient establishes a new relationship with a hospital or a primary care physician, a relationship of trust could be granted by default to the primary care physician and/or their practice or establishment. Therefore the billing departments, the claims adjuster, the other physicians associated with the healthcare establishment or practice may also, by default, inherit access to that end-user's medical records, as well as access to certain managed features. This obviates the untenable process of needing to individually select and add permissions each time a change is made or a new relationship of trust is established with a different practitioner, practice, caregiver or service provider. It should be evident to one of ordinary skill in the art that establishing such granularity of levels of trust on a per-patient, per-service provider basis would not scale well, where many consumers and service providers are to be enrolled. Thus, by using default profiles of established trust, and allowing inheritance of trust, unauthorized access to files is prohibited while still allowing ease of access to those who do genuinely need access to the information.

The invention of the subject Patent Application is preferably operable to manage and capture user access, data access and security rights within a healthcare management network. The core security model of this framework is preferably based on three elements: Principals, Roles, and Relationships. By using these three elements, the framework effectively defines the social interactions between entities within the system and effectively manages data and access security across the framework.

Preferably, the core security model also uniquely models the natural human interactions between entities creating an intuitive "trust" security model allowing entities to inherit data and access rights within the system. This inheritance model also helps to scale system security to many users, because entities may then securely interact with each other through this inherited security model, since each entity assumes its natural security rights based on their role within the system.

Principals are the entities that interact within the system. Principals may be individuals, organizations, or service accounts. This abstraction allows for further flexibility for other principal types, including, but not limited to software agents or clients, healthcare networks, plan design, and other uses that may be defined as an entity and may functionally interact with other principals.

A relationship is a link between two principals. Relationships may be uni-directional between the owner principal and the related principal. The relationship may also define the role that the related principal plays for the owner principal.

For a real-world example: a relationship may exist between a person, John Smith, and his company, ABC Inc. In the system, this relationship would be defined as two relationship records: One record where John Smith is the owner, ABC is the related principal, and the role is Employer; and a second record where ABC is the owner, John is the related principal, and the role is Employee.

Relationships define how trust or security should be defined between principals. This trust relationship is further refined with "roles." As an example, defined relationships allow for enforcement of privacy rules and regulations such as HIPPA in the health industry.

Roles may define and characterize the type of relationships between two principals. When a principal is associated with a role, the principal is expected to use the characteristics of the role to perform functions within the system. Particular characteristics defined by roles in the system include, but are not limited to: security rights to application features, permissions to interact with other principals, and context-relevant data properties of a principal. An example is a "Doctor" role. Doctors may have access to special software features that are only relevant to the functions of a Doctor role. Doctors are permitted to access electronic medical record modules that other principals may not. Doctors may be able to interact with their own patients in ways that they cannot interact with other principals of the system, such as modifying their patients' medical records and sending medical alerts. Doctors may be afforded properties such as specialty, office hours, and national physician code that are not applicable to other roles.

Some roles are independent of relationships and control the functions or rights that a principal may claim to use. Other roles may be used in relationships. Relationship roles may also have natural inverses. For example, "Doctor" and "Patient" are inverses of each other, which help further categorize and characterize the security between Principals.

Features within the systems may be similar to industry standard definitions of software features; they may define what a user may do with the system. Features are used to specify security and to extend the system. A notable aspect of the present invention is that features may be explicitly named and registered within the system independently of the platform's core.

The full range of features and services may not be defined at design-time. Therefore, the system allows features to be added to the system after the implementation of the platform, for instance, at the time of deployment or even during run-time use. Service Operations that a feature requires for proper operation may also explicitly be associated with features.

Using all the objects together in the security model allows the system to calculate access control lists. These lists are used by the system to check user access to particular service operations from particular clients. Preferably, the above security model is defined with records database systems and other support files in the system such as XML and binary code.

Provision is also made for security of information in transit through encryption by providing secure sockets layer (SSL) or transport layer security (TLS) to provide hypertext transfer protocol secure (HTTPS). Other means to secure the connection, as may be known to one of ordinary skill in the art, may be employed to prevent eavesdropping and man-in-the-middle attacks. This generally assures safe transit from point A to point B.

To ensure that the servers' data store and various databases are secure, servers are firewall protected, having very limited administrator access and only ports that are necessary will be open. Other means, as generally known to one of skill in the art may be employed.

The present invention may also provide for internet communications capability allowing for near real-time exchanges between two or more parties through an on-line connection. This may be useful in allowing end-users, patients, or consumers to chat with healthcare professionals, claims adjusters, practitioners, or other service providers.

Figure 3:
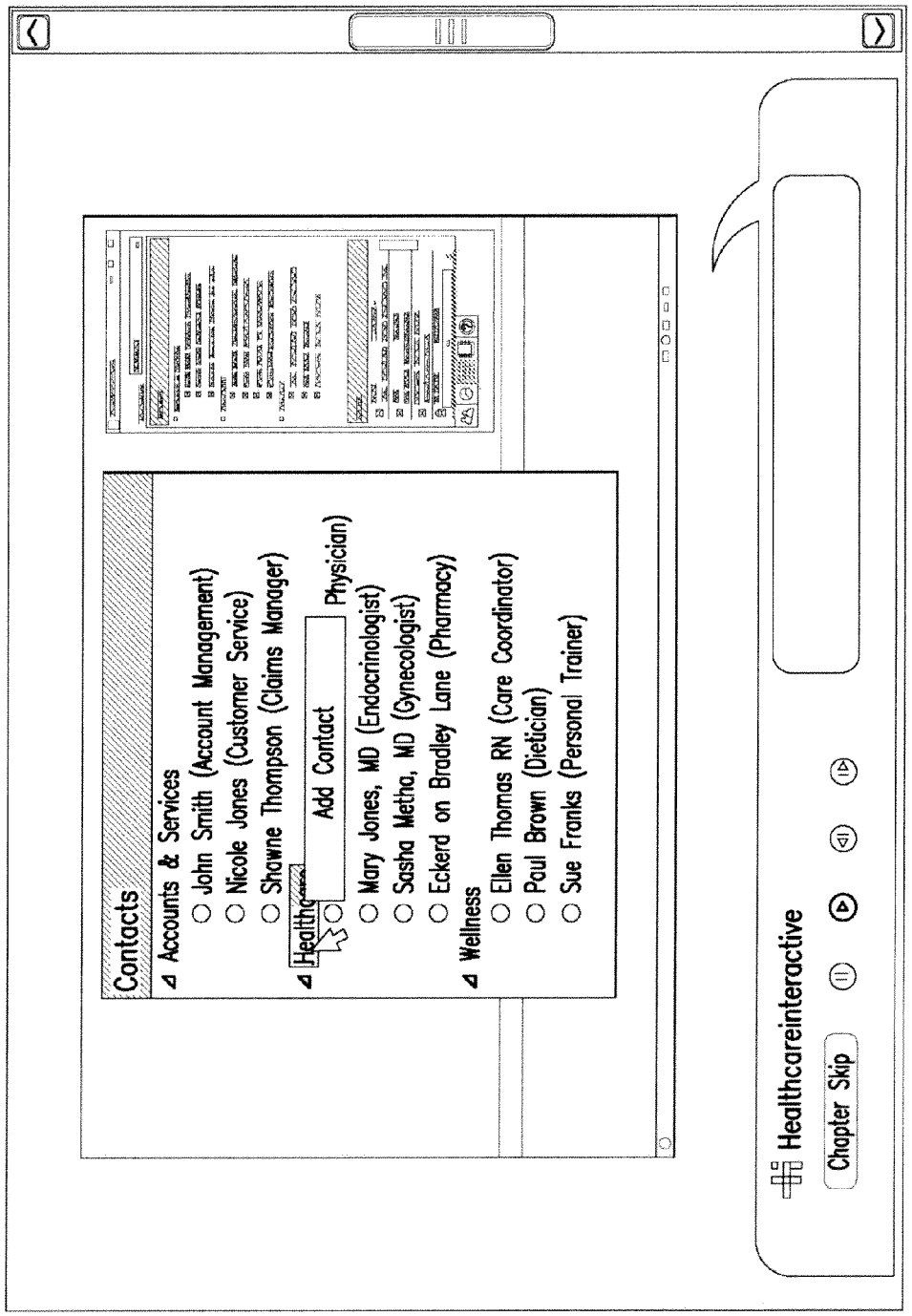
FIG. 3 is an illustrative example of a display of a graphical user interface of an application of an exemplary embodiment of the present invention.
Figure 4:
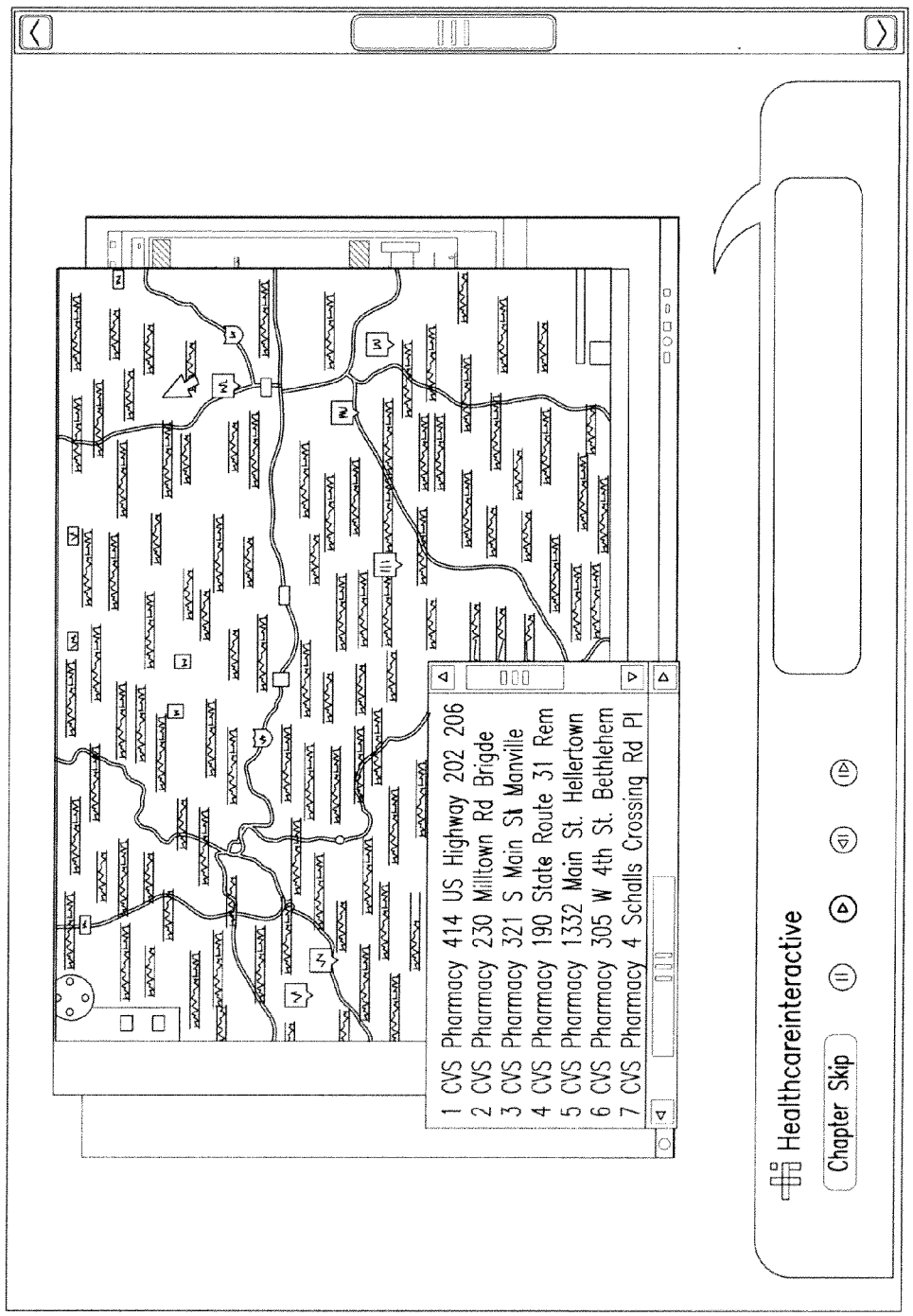
FIG. 4 is an illustrative example of a display of a graphical user interface of an application of an exemplary embodiment of the present invention.
Figure 5:
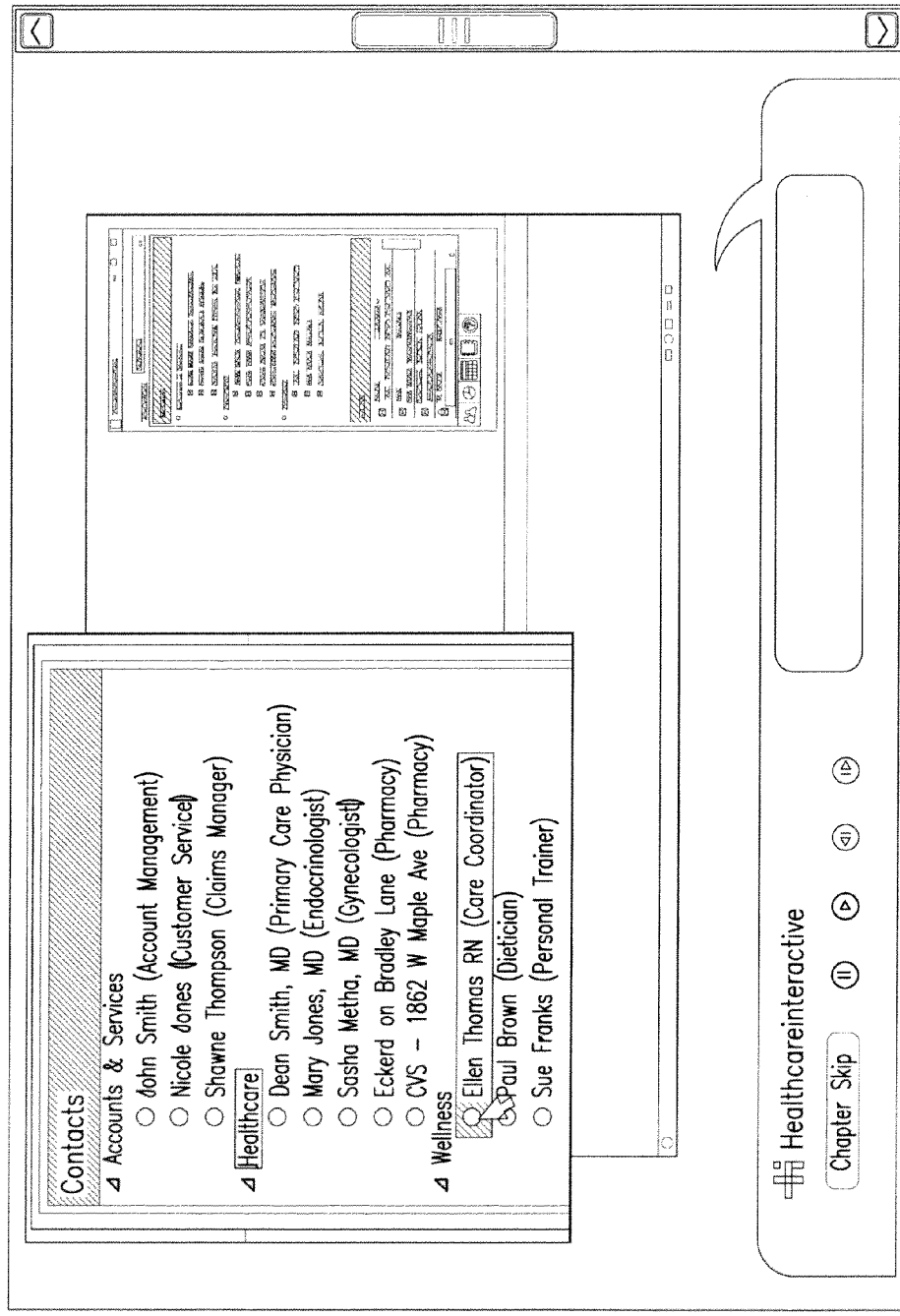
FIG. 5 is an illustrative example of a display of a graphical user interface of an application of an exemplary embodiment of the present invention.
Figure 6:
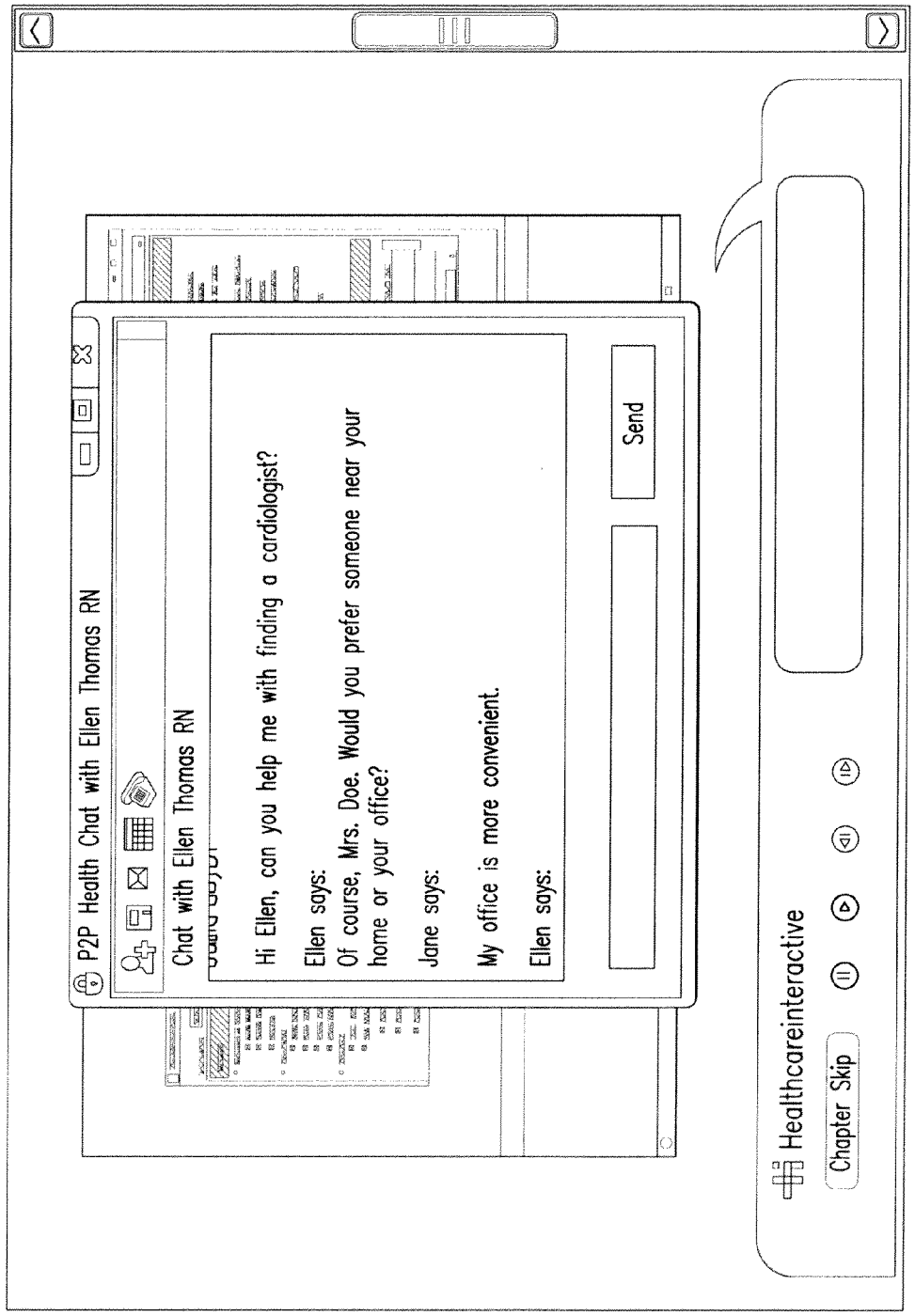
FIG. 6 is an illustrative example of a display of a graphical user interface of an application of an exemplary embodiment of the present invention.

As is seen in FIG. 6, an end-user, for example Jane, could initiate a chat with a registered nurse to find a specialized caregiver. Likewise, and as seen in FIG. 3, each end-user maintains a list of contacts. The contacts are broken up into specialized categories such as accounts and services which could illustratively include an account management contact, a customer service contact, or a claims manager contact.

Another category may be healthcare professionals which could include a primary care physician, specialists such as an endocrinologist, a gynecologist, or a pharmacist. Another category could be a wellness category including a care coordinator, a dietician, or a personal trainer. An end-user is able to establish contact with any of the contacts on the contact list using any number of different communication methodologies including a chat program, a message program, or any other means, such as Voice Over IP (VoIP) or a video conference.

In the event that a specific contact that is trying to be reached is not available or is not connected, the server will enqueue messages to that recipient and store them on the server until such time as that recipient does log on. When the intended recipient does log on, the server then proceeds to send the queued messages to that recipient.

Each end-user will be provided with the ability to manage their contact list of relevant healthcare services. Included in this ability to manage the contact list is an ability to organize contact for easily initiating communications, categorizing by service functionality or relationship to the end-user consumer.

A goal of this interface is to keep the interface simple and easy to use, such that it may be used by potentially any type of end-user, including the elderly, children, or handicapped individuals. Rather than a more promiscuous-type approach of other social-type networks, the healthcare network of the subject Patent Application is relatively more exclusive in that only contacts that are relevant, or necessary, or that meet certain criteria are allowed to be added as contacts. This will reduce the incidence of spam and unsolicited advertisements and increase a general overall security of the system.

For example, an end-user's ability to simply add another end-user into the contact list is preferably restricted to ensure security and reduce occurrence of unwanted, unsolicited communications. To further security, practitioners or service providers may not be able to simply add individual end-users, or consumers, to contact lists. Instead, the end-user may be required to first add the healthcare practitioner or service provider to the contact list. By having the end-user, or consumer, initiate communication, security is enhanced and spam, or unsolicited advertisement type material, will be restricted, thus allowing end-users to focus more exclusively on more pertinent, relevant, and important messages from authorized service providers. By constraining the contact management and contact lists to be as simple and familiar or intuitive as possible, the effectiveness of the contact list and the healthcare management application in general is enhanced.

Another capability provided by the healthcare management system is alerts. Alerts are messages generally sent between consumers and healthcare professionals or from a professional to another professional.

Figure 7:
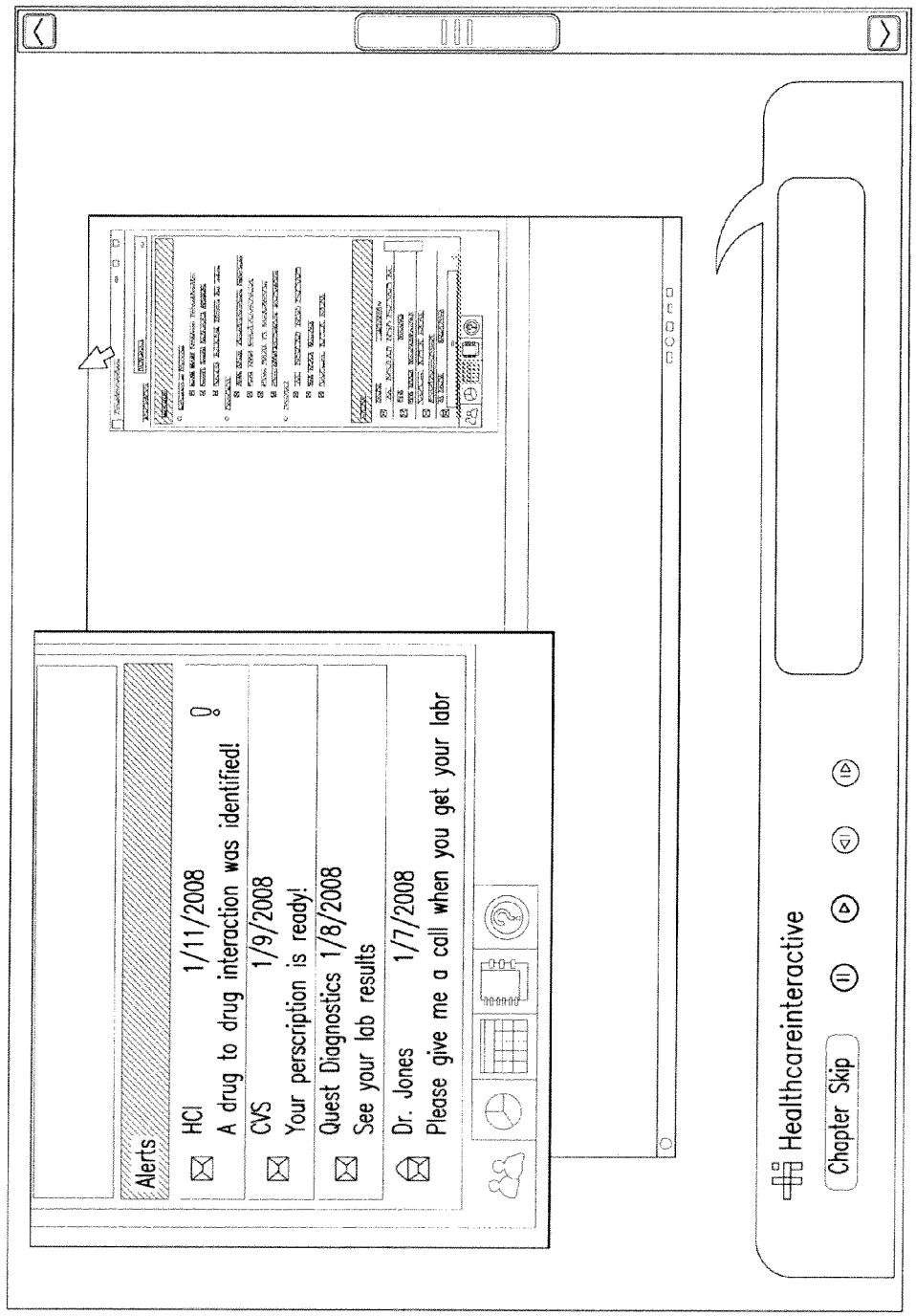
FIG. 7 is an illustrative example of a display of a graphical user interface of an application of an exemplary embodiment of the present invention.

As is illustrated in FIG. 7, alerts may be enqueued and presented to a user in a variety of formats including a threaded or a wall-type presentation of tabulated alert events. The tabulated alerts list presents a brief subject, date or time, and a brief excerpt of the subject matter of the alert. A user may optionally activate an individual alert to be provided with the full information on the alert. As is seen, a plurality of different caretakers or service providers or practitioners are able to insert and provide alerts to an end-user to aid them in their healthcare management.

Alerts may be messages initiated by the system itself, for instance as outcomes to rules that check for preconfigured settings. For example, the healthcare management system of the subject Patent Application may be notified or may itself monitor and observe that a new prescription added was for a brand named drug which could trigger an alert to alert the user that a generic drug is available.

Alerts may be enqueued where an immediate response is not required. While alerts may behave in a manner similar to messages, there are differences. For instance, alerts may be constrained completely within the system which would allow for more secure transmission and system tracking. A combination of visual, auditory, or haptic indicators preferably inform a receiving party of the arrival of a new alert. Indeed the entire queue of incoming alerts and/or messages may be tabulated in an incoming wall or a thread, or any other suitable method known in the art.

Yet another functionality provided in the healthcare management system of the subject Patent Application is a reminder function. The reminders may illustratively be requests for action at a specific time or times. For example, a reminder would be used to remind an end-user or patient that there is an upcoming six month checkup that they should attend. Reminders may be set up by an end-user, by a practitioner or service provider, or may be system initiated. A combination of visual, auditory, or haptic indicators may announce to an end-user that a reminder needs attention at a particular time or times. The reminders may be personalized based on the patient's current healthcare experiences. For example: checkups, follow-ups, appointment reminders, or yearly review of claims, any of these may serve as a basis for a reminder. Reminders or alerts may be further customized based on a user's psychographic profile using message ranking methodologies to more effectively communicate with a user.

Message ranking utilizes data-driven or Evidence Based Messaging (EBM) and is used as a mechanism within the Healthspace framework of the healthcare management system of the subject invention to improve the efficiency of messages, alerts, reminders, and communication in general. After segmenting a population of interest using latent class modeling based upon behavioral, psychographic, demographic, etc. data, and being able to accurately classify individuals into segments using a handful of key questions that form a typing tool, it is often useful to study target segments for the purpose of optimizing the effectiveness of messaging or communications. Data Driven Messaging (DDM) is a modeling technique that results in the identification and creation of multimedia (text, visual, audio) communications tailored to the preferences and needs of one or more target segments.

To make the communications or messages more efficient, statistical methodologies are used to compare and select message elements, ordering of content, imagery, colors, audio-visual content, and the selection of supporting materials to be the most effective for a given segment. This helps alleviate the inherent problem of messages being ignored, misconceived, misunderstood or misinterpreted.

Initially, a statistical design for a question is created. The design results in multiple sets of cards, each card representing a group of questions to be asked of a respondent. For example, a question may be: Which of the following attributes of a physician do you consider to be the least important and which do you consider to be the most important?

The results of a Maximum Difference Scaling (MDS) question are prepared and analyzed. The resultant data produces a scored list of attributes. The scores are such that if the attributes were chosen at random to be most important and least important, all attributes would have a score of 100—the average score. Scores below 100 are therefore interpreted as having below average importance, while scores above 100 have above average importance. The farther a score is above 100, the more important it is. This methodology will thereby provide a relative ranking of attributes, and a pseudo-absolute rank scale of attributes. That is, if one attribute is ranked as most important, the magnitude of the difference between its score and the next highest score reveals how much more important the one attribute is. As an example, being board certified (score=210) is the most important physician attribute to the sample of respondents, but it is not much more important, if at all, than the physician having evening hours (score=200).

This allows for leveraging segmentation results to isolate homogeneous groups within a population, allowing for further segment-specific research, for example: data driven messaging. A further benefit is that effective communication is achieved such that information relayed is clear, understandable, and as believable as possible, towards the goal of convincing an end-user to adopt suggestions, change behaviors, or be mindful of potential issues.

For example, a segmentation could be performed on patients with diabetes if a health plan wanted to improve treatment compliance among members of a segment that were not managing their diabetes well and were at risk for complications. Data driven messaging, in the context of the health care management system, would enable the testing and refinement of a variety of differently tailored messages, specific to each segment, optimizing the language used to explain the risk of non-compliance, descriptions/graphics/images of potential complications, amount and quality of technical information ranging from broad descriptions/generalizations in lay terms/articles from medical journals or graphical presentations of clinical data.

Continuing the Diabetes example: Data driven messaging will provide quantitative evidence of elements of messaging such as, what information needs to be communicated, how information must be communicated, and in what sequence it needs to be communicated in order to optimally motivate the target segment of diabetes patients to: increase treatment compliance, reduce the risk of complications, increase their health efficiency index, lower the cost of their healthcare, and reduce number of sick days, etc.

Prioritizing message order allows for getting the subjectively most important factors or elements of a message to a particular segment first to thereby securely capture readers of the particular segment such that they will understand and be motivated by the entirety of the message. For example, where it has been established through results of the maximum difference scaling questions, that one attribute is most important, this attribute may be emphasized and displayed most prominently. Still further, the relatively less important attributes may be communicated in their respective relative order of import to maximize impact. For example, if three elements of an insurance plan were found to be crucial to the plan's adoption: cost of the monthly premium, immediate access to specialists, and $10 Rx copays. One segment considering plan adoption may rate all three items as necessary in their choice of a plan, but may prefer to know about the costs of the plan up-front. On the other hand, these three plan attributes may be equally important to another segment which is also cost-sensitive, but be secondary to the option of having immediate access to specialists. If this information is known, the order of the message elements may be adjusted to maximize impact.

Still further, this data driven methodology allows for minimizing distractions or noise created by communications that are unclear or ineffectual. With data driven messaging, potential communications are tested, results analyzed, and then optimized to appeal (in terms of preference, motivational power, clarity, etc.) to a targeted segment. This form of sending tailored messages with calculated content fosters acceptance of messaging, reliance thereon, changed behavior, and ultimately, a more efficient healthcare system.

This data driven messaging methodology may be applied to all messages sent by the system including customer service, physician management, evidence based medicine or clinical protocol management, medical management, disease management and behavioral health management.

As an example: in medical management, utilization review and case management: patients with complex medical conditions, co-morbidities, multiple doctors and medications require not only review and coordination of care, but also constant communication between the case manager and physician, case manager and patient, and physician and patient. Giving the case manager insight into the communication style and content hot buttons of the physicians and patients they are coordinating will improve coordination and teamwork of all parties involved in a particular case.

As another example: in evidence based medicine or clinical protocol management—reviews of claims and treatment history may reveal whether standard protocols are being followed in the care of individual patients both with acute or chronic conditions, and when it comes to preventive medicine recommendations. Once this information is gathered on the back-end, suggestions and/or intervention messages are sent to the physician and/or patient. Informed communications through data driven messaging help create messages that are more likely to be acted upon, thus improving health.

Still further, physicians may be segmented, with target segments studied and targeted using data driven messaging techniques to improve patient care, increase efficiency, help align treatment protocols most closely with current standards of care, etc.

Figure 8:
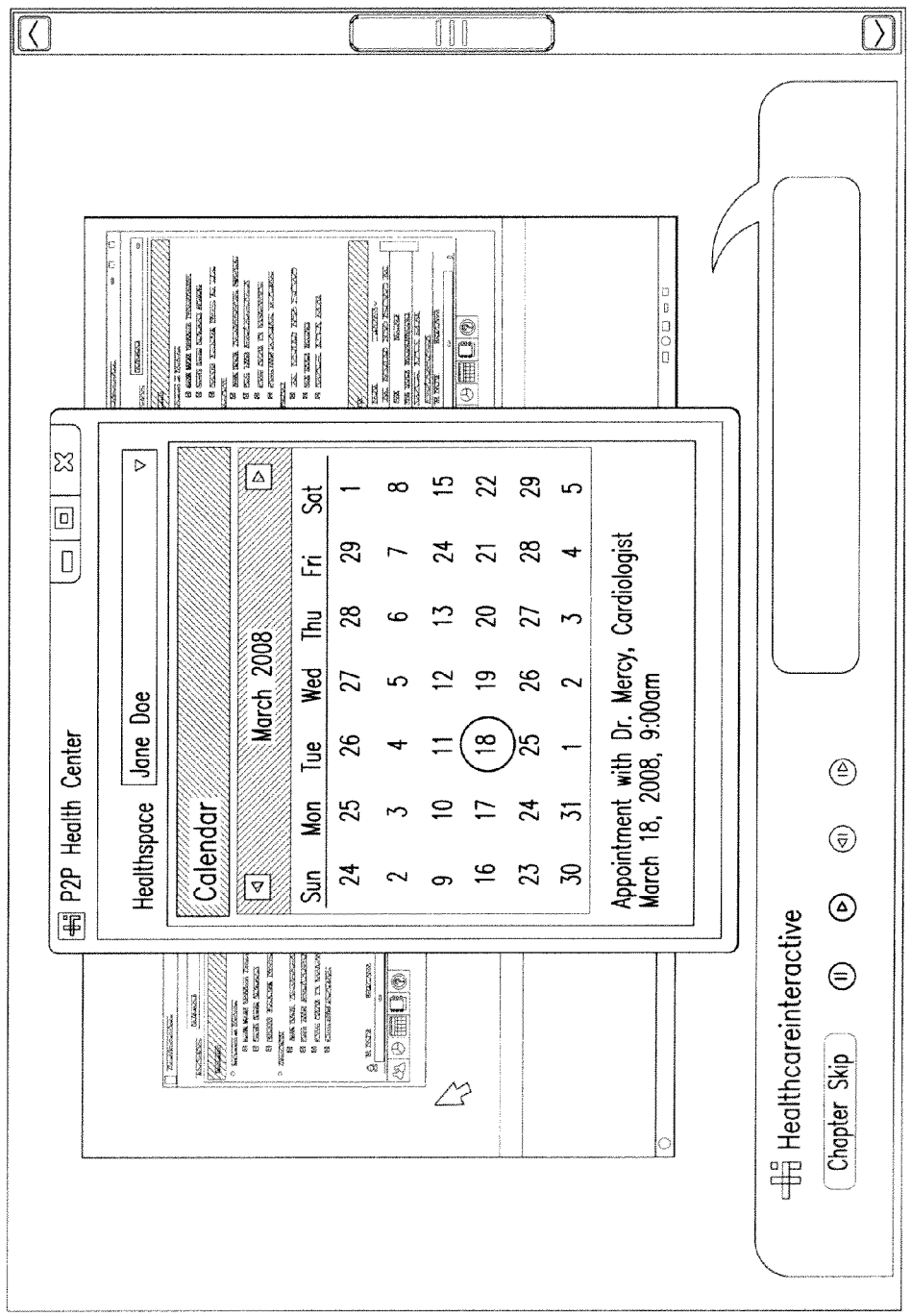
FIG. 8 is an illustrative example of a display of a graphical user interface of an application of an exemplary embodiment of the present invention.
Figure 9:
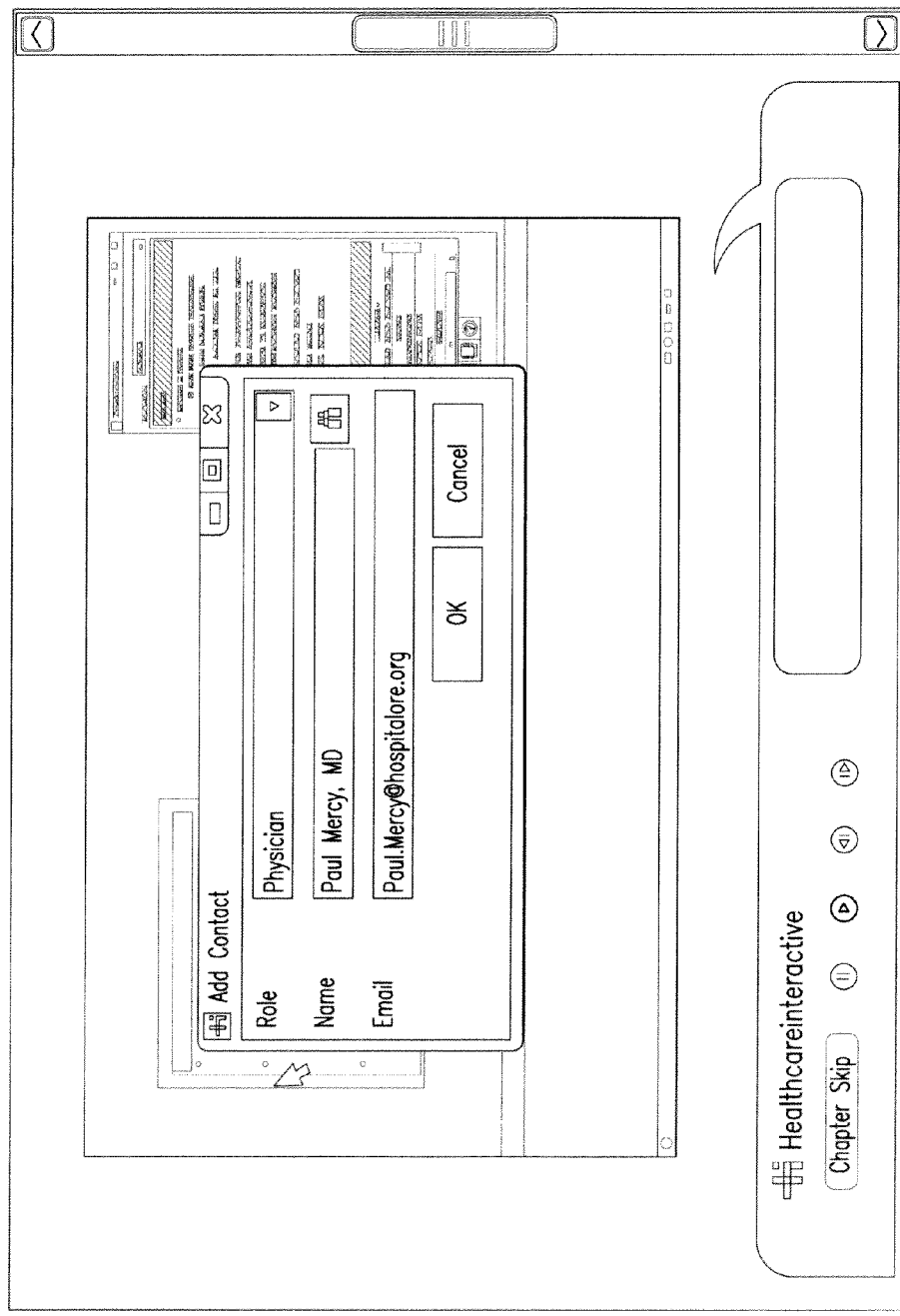
FIG. 9 is an illustrative example of a display of a graphical user interface of an application of an exemplary embodiment of the present invention.
Figure 10:
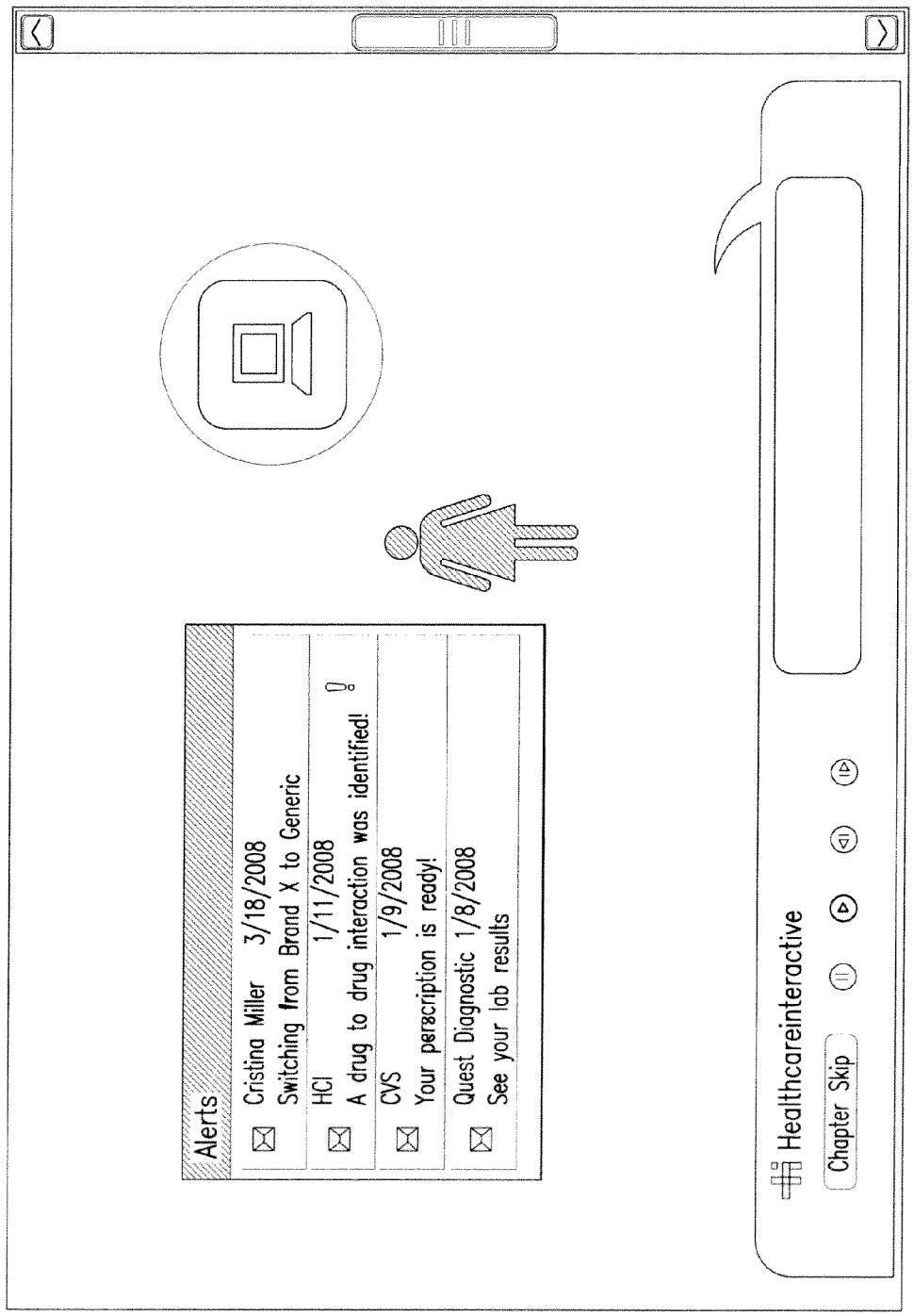
FIG. 10 is an illustrative example of a display of a graphical user interface of an application of an exemplary embodiment of the present invention.

As seen in FIG. 8, another functionality the healthcare management system provides is calendaring. The healthcare management system of the subject Patent Application preferably maintains customized calendars for each end-user. Reminders and alerts are tied in to each end-user's calendar. Each end-user is able to populate their calendar with important healthcare related events, dates, or appointments. Also, service providers may be able to input events to a user's calendar. Each end-user's calendar is a personalized calendar, being personalized based on the patient, and focused on healthcare related appointments or events. The calendar illustratively lists appointments or highlighting of time-critical messaging including doctor's appointments, medication refills, or drug-to-drug interactions.

At a service provider level, the healthcare management system provides for assistance with coordination to avoid schedule conflicts. The assistance may be in the form of notification, reminders, or alerts of scheduling conflicts or of upcoming scheduling appoint type events. Preferably, caretakers, service providers, and other authorized users could input events and/or reminders to a user's calendar automatically and without requiring the end-user or patient to perform anything. Alternatively, the client or end-user could be given a chance to authorize or deny service provider's proposed additions, subtractions, or modifications to that end-user's or other authorized accounts' calendars.

In an illustrative view displayed at a user interface, an end-user, patient, or consumer may add a physician to her network, including the physician in their contact list, and then contact a care coordinator to secure an appointment with a new physician. A caretaker could then populate the consumer's calendar with the appointment and all relevant information which could trigger corresponding alerts and/or reminders to the user.

Preferably, there is a specific or customized view presented for one type of end-user such as a patient, or consumer, and there are alternate views presented for differing types or species of end-users such as a caregiver, human resources personnel, or claims adjuster. The type of interface is determined by the type of user, potentially being role-based, so there is a correlation between a type of user and a type of interface that will be presented to them.

Illustratively, there are two main types of users: consumers and service providers. Consumers will generally view only their own information and manage their own interfaces. However, there may be exceptions where a consumer is able to access another consumer's data and manage their calendar, alerts, reminders, or contact list. This could generally be provided for a husband accessing a wife's data; a wife accessing a husband's data; or in the case of parents: accessing and managing their childrens' data. Some illustrative examples of consumers' views could be a patient/employee view, an employer view, or an out-of-network health service provider view.

While consumers generally view their own information, service providers may be able to manage the information of consumers or other service providers. Some exemplary service provider views could be: a customer service representative view, an account services representative view, a care manager view, an executive/system administrator view, or an in-network health service provider view. Some service providers may not be provided with access to any particular consumer's data, and instead are provided only with aggregate or abstracted data.

Still further, consumers or service providers may be provided with a default view or a universe of potential views of information or functionalities, and the consumer or service provider is able to customize the view utilizing a subset of the available information or functionality that they are authorized to access.

Figure 21:
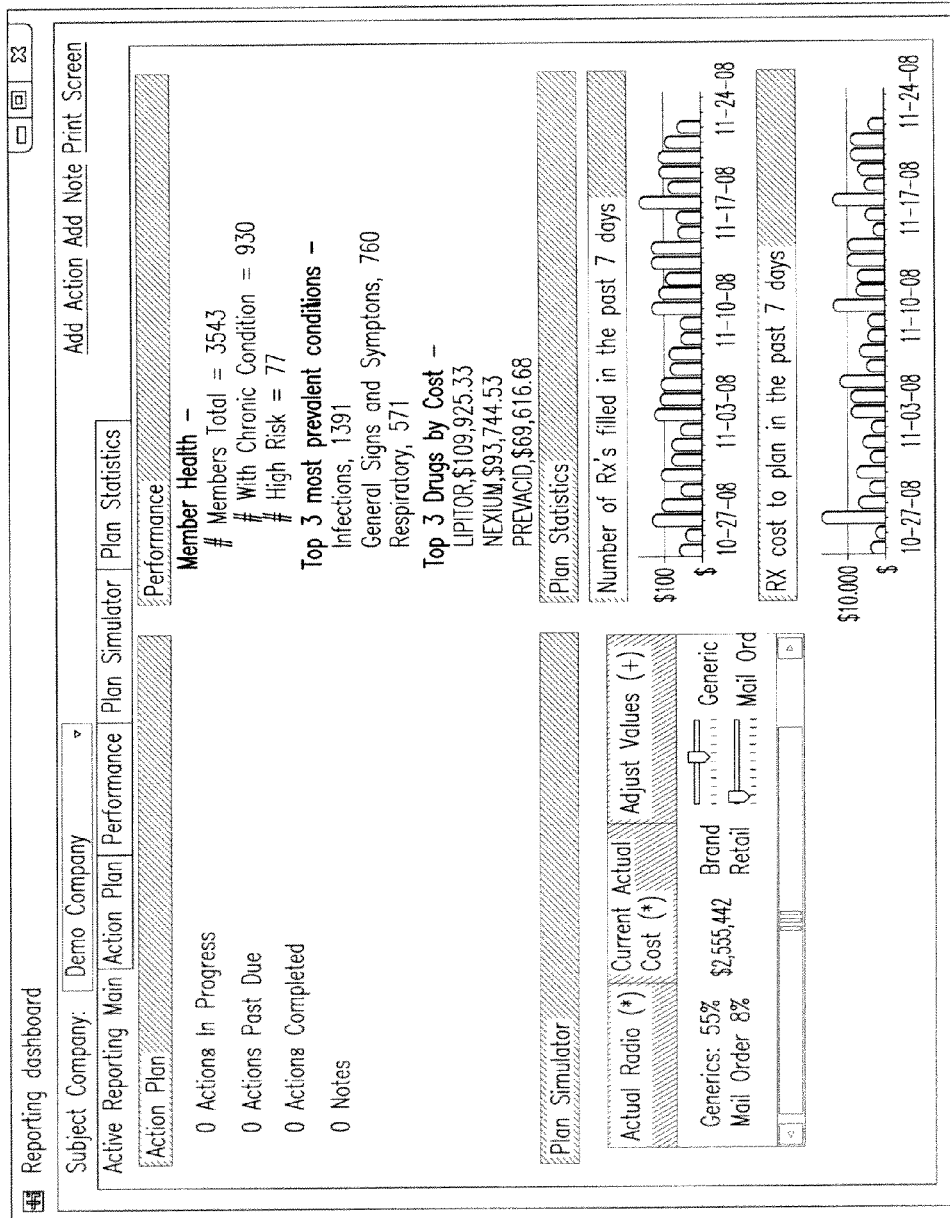
FIG. 21 is an illustrative example of a display of a graphical user interface of a second application of an exemplary embodiment of the present invention.

A customized view, as seen in FIG. 21, prepared for administrators using aggregate or abstracted data may be implemented with another client program using the Healthspace framework API, as part of the health care management system, such as Active Reporting Service (ARS), which organizes and evaluates pharmacy and medical data and combines management, measurement, and administration tools on the front-end within the confines of the Health Insurance Portability and Accountability Act (HIPAA). ARS allows management or administrative staff to receive pertinent information to identify problems and find custom solutions that will lead to alternatives, choice and competition by looking at aggregate health benefits information for groups relevant to the particular administrator or manager. ARS provides for live plan performance; real-time plan simulation; actionable turn-key outreach, measuring results and making adjustments. This allows for a collaborative environment where a plan administrator/manager, consultant/broker, and account management team work together to find key health costs and condition metrics, analyze this data and interpret to simulate plan changes and estimate costs, plan Return On Investment (ROI) models, and utilize trending information to measure the effects of program changes and see how a health program is developing over time.

Another functionality that the subject Patent Application provides for is an information portal which includes a research tool to look up trusted healthcare resources in exploring various healthcare concerns. Still further, a consumer is able to view their claims history or an aggregate reporting of healthcare usage, or even further, access a predictive modeling or health risk assessment library or information knowledge base.

A healthcare efficiency rating or scoring functionality is provided to display an efficiency rating or score of an individual based on their healthcare decisions and participation. This rating or score is compared to bench marks or peer groups, as defined by the individual consumer's peers at a place of employment or based on peers decided by factors such as age, sex, body biometrics or even fellow patrons of a particular service provider. The Healthspace efficiency index, rating, or scoring is utilized to maximize health benefit utilization or maximize healthy living or wellness or maximize treatment plan adherence and compliance. The Healthspace efficiency index is used to incentivize or penalize consumers (or even, potentially, service providers) towards certain kinds of behaviors.

Preferably, a consumer's user interface has a portion of the screen devoted to prominently displaying the efficiency index which prompts them to click on it which explains to the consumer that the efficiency index helps a particular consumer understand how to better improve their quality of life and better manage their cost of care. Illustratively, the user is presented with expert recommendations from their healthcare touch points or contacts to help them maximize their health benefits.

Figure 11:
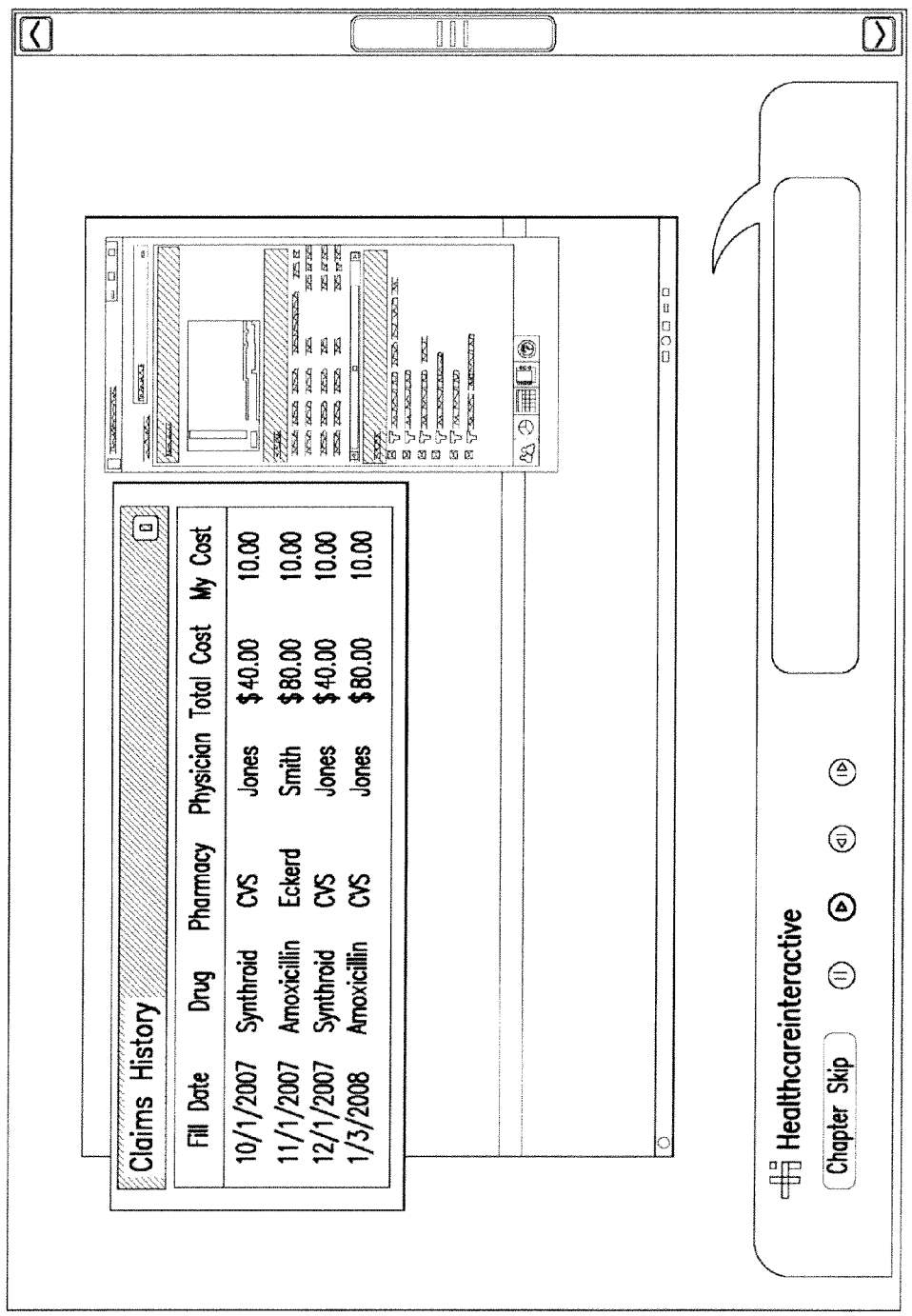
FIG. 11 is an illustrative example of a display of a graphical user interface of an application of an exemplary embodiment of the present invention.

An exemplary way of doing this is that the user is presented with an alert from a pharmacy benefit manager stating that the consumer's recent visit to a practitioner resulted in a prescription of a brand named drug, and that switching to a generic drug could save the consumer money and increase their efficiency index. To motivate the user to increase the efficiency index, certain incentives may be provided, for example: the consumer may be provided with a zero co-pay for the first month. Accordingly, and as seen in FIG. 11, a user's claims history is preferably presented to them, along with an efficiency index.

Providing the user and administrators with an efficiency index allows for quantitative analysis of plan utilization customized to the specific population. This allows plan administrators to identify weak points in coverage, compare their plan with other plans (as applied to their users), and identify areas of potential savings based on the plan document. Potential savings could be based on generic pharmacy availability, pre-certification requirements, or matching in-network doctors with specialties. The efficiency index enables the plan administrator to identify an overall plan spectrum or fingerprint, quantitatively evaluate plan performance, and create customizable suggestions. This wealth of information may be used to target excessive denials from particular exclusions which results in high costs including increased absenteeism and detriments to users' health. Further, marketing opportunities become apparent to administrators when viewing efficiency information in the aggregate. Based on the quantitative analysis, an administrator is able to restructure the plan accordingly to further optimize costs and benefits according to their unique group of users. Not only are administrators able to optimize the plans, but individual users are able to monitor their own efficiency indices and change their behavior to be more healthy and save money.

Figure 12:
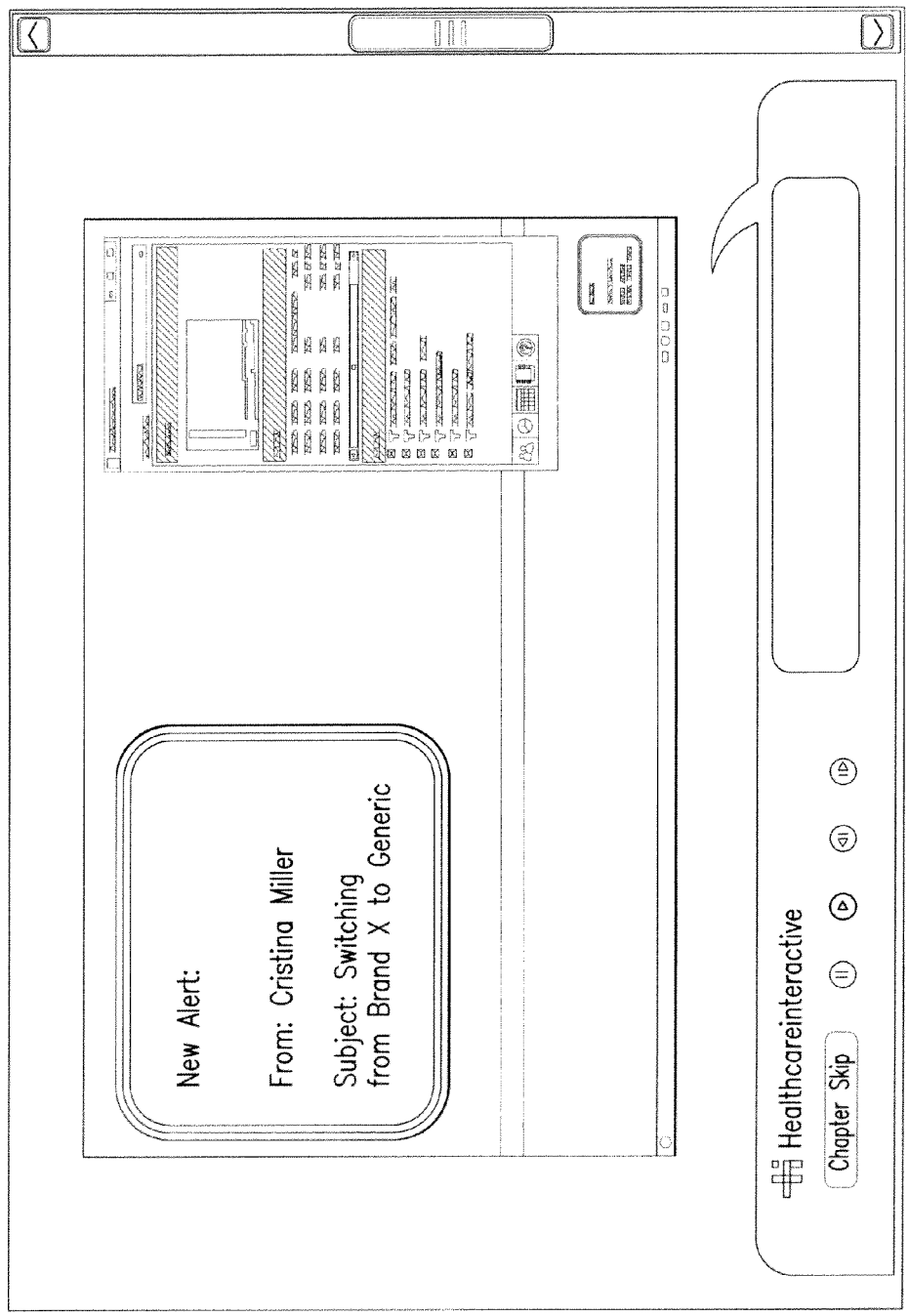
FIG. 12 is an illustrative example of a display of a graphical user interface of an application of an exemplary embodiment of the present invention.
Figure 13:
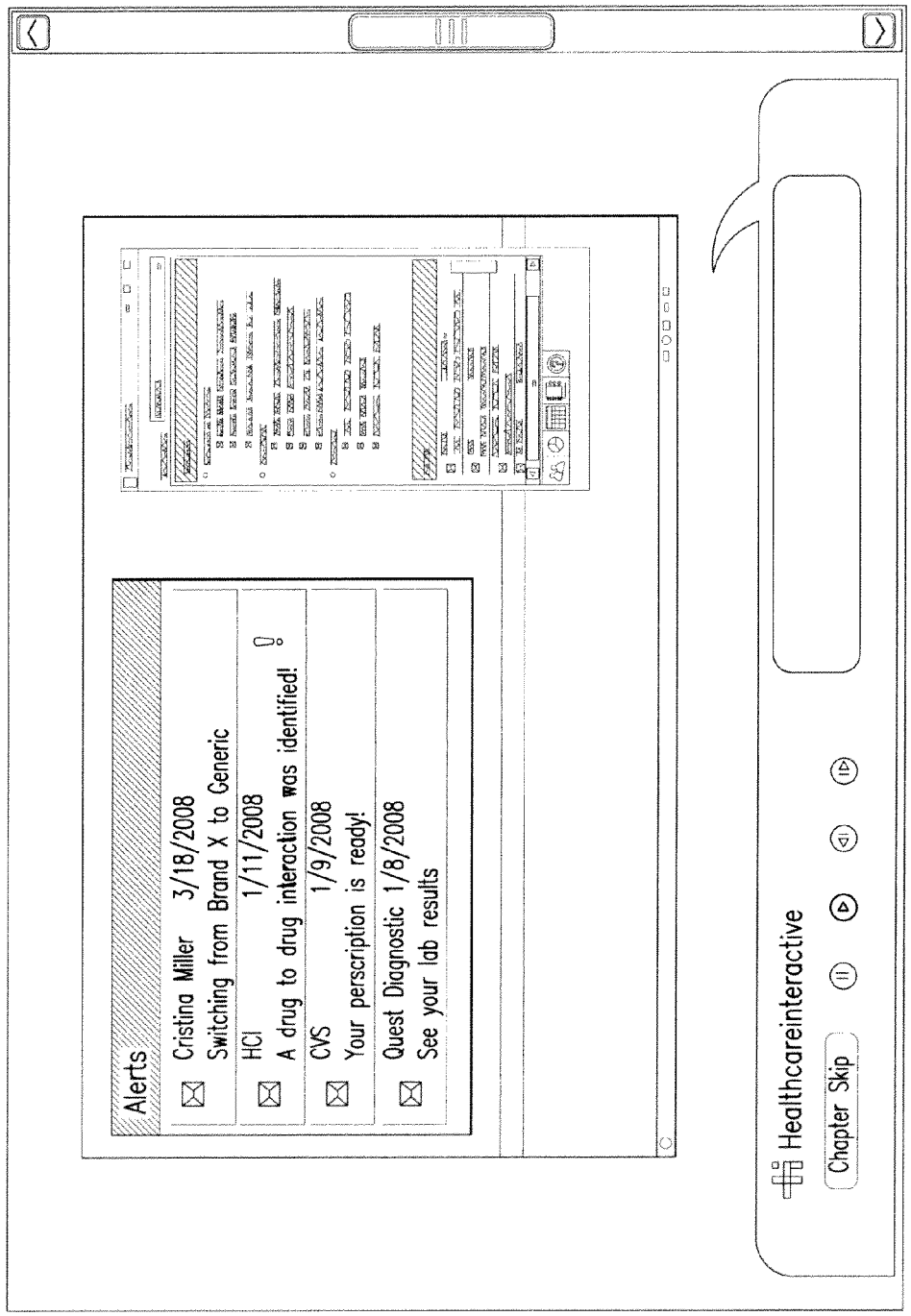
FIG. 13 is an illustrative example of a display of a graphical user interface of an application of an exemplary embodiment of the present invention.

As seen in FIG. 12, the efficiency index, or rating is presented to the user and were the efficiency index or rating not acceptable to the user or if the user desired to increase the efficiency rating, the user may be prompted to follow expert advice. For example, as seen in FIG. 13, the user is presented with an alert from a service provider advising them of a course of action to improve their efficiency rating.

Figure 14:
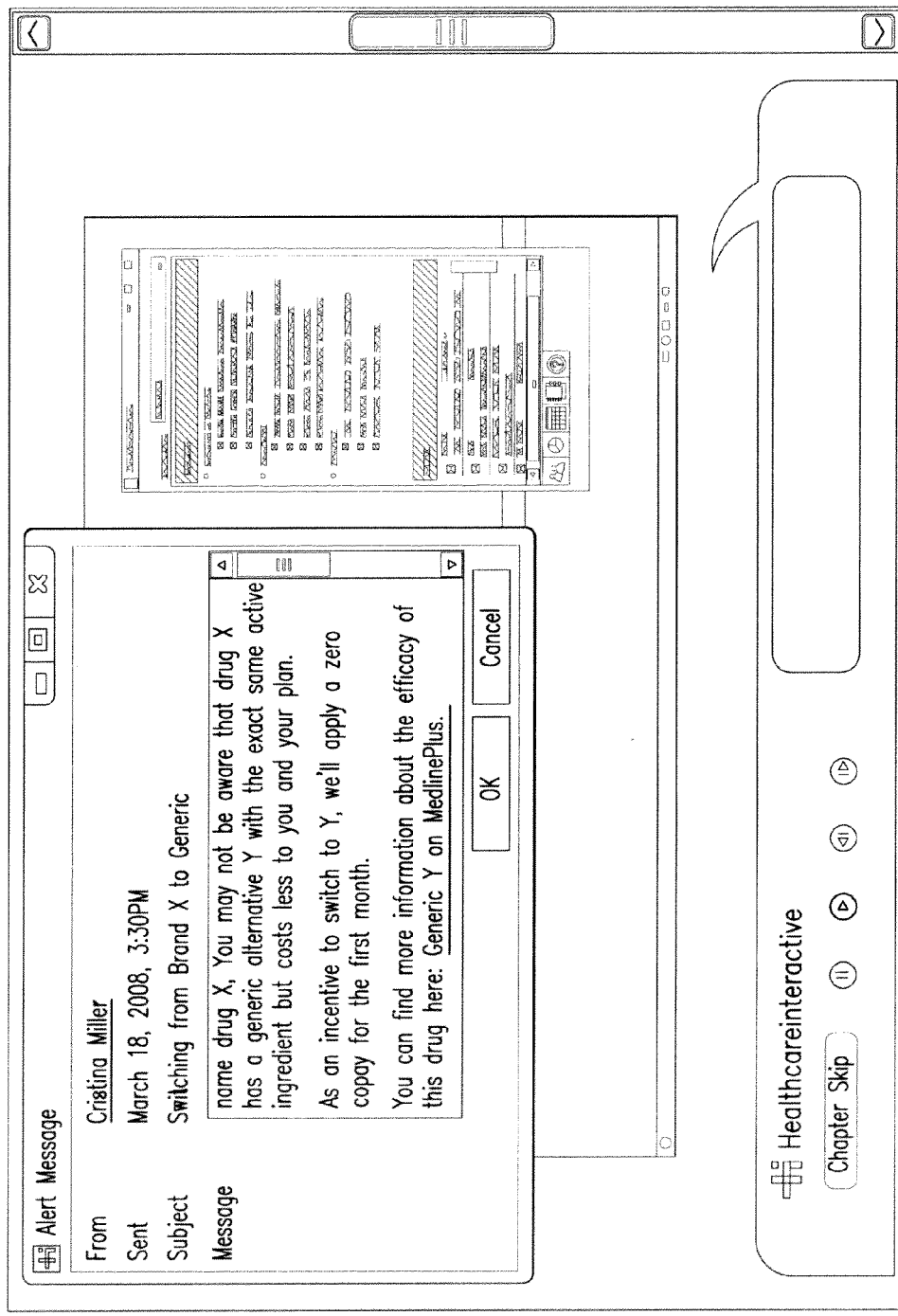
FIG. 14 is an illustrative example of a display of a graphical user interface of an application of an exemplary embodiment of the present invention.
Figure 15:
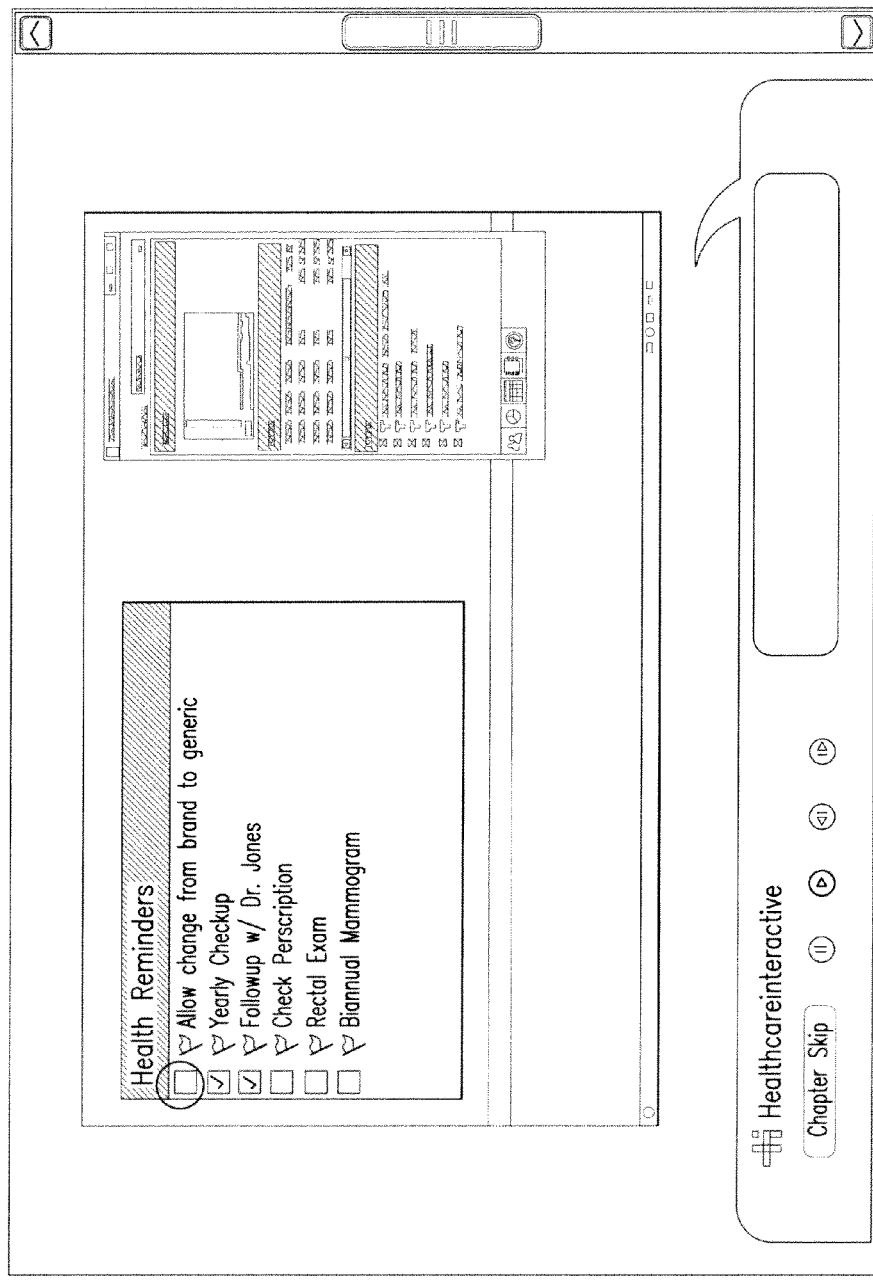
FIG. 15 is an illustrative example of a display of a graphical user interface of an application of an exemplary embodiment of the present invention.
Figure 16:
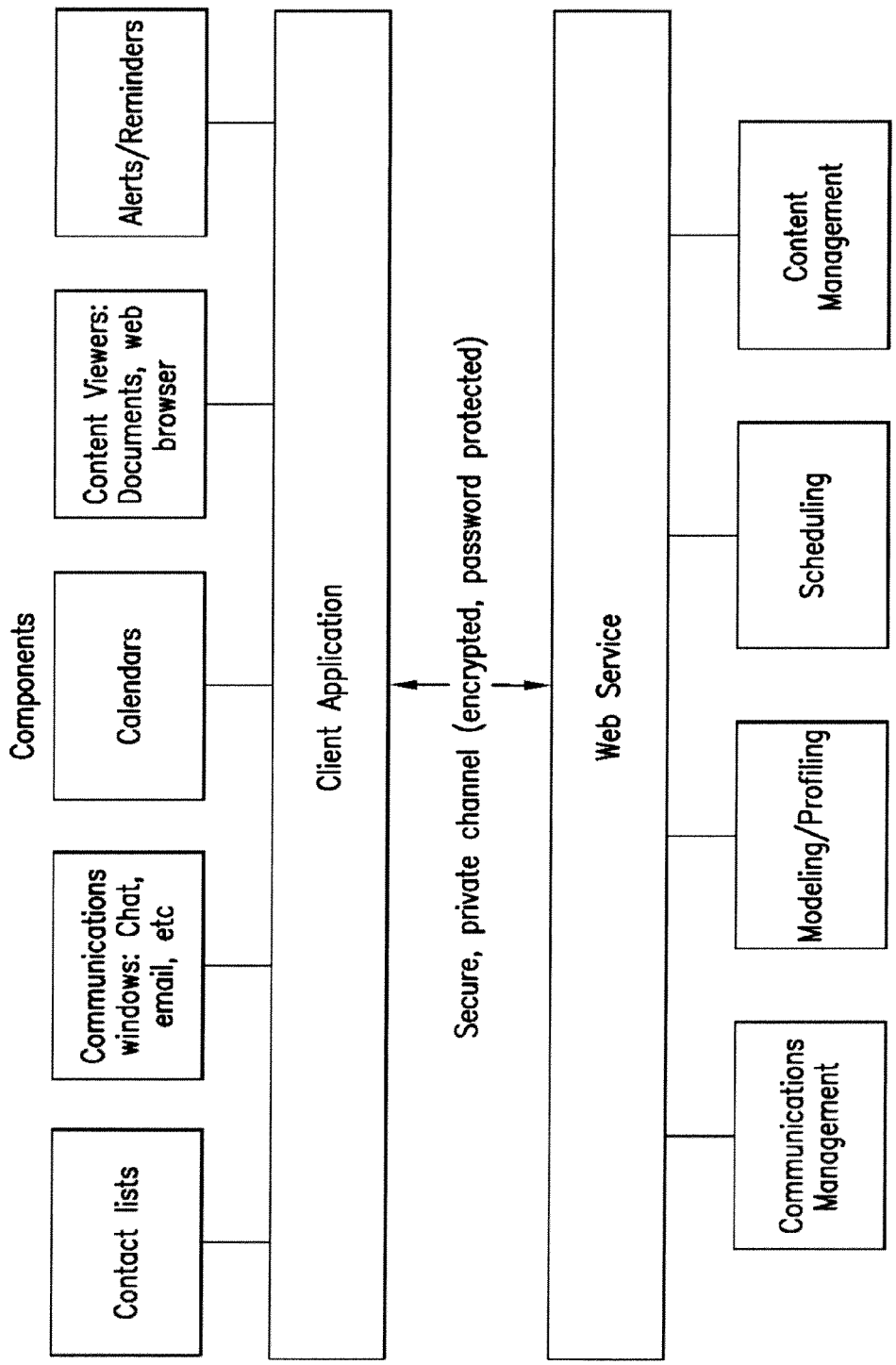
FIG. 16 is a diagram schematically illustrating a functional arrangement of system components in one exemplary embodiment of the present invention.
Figure 17:
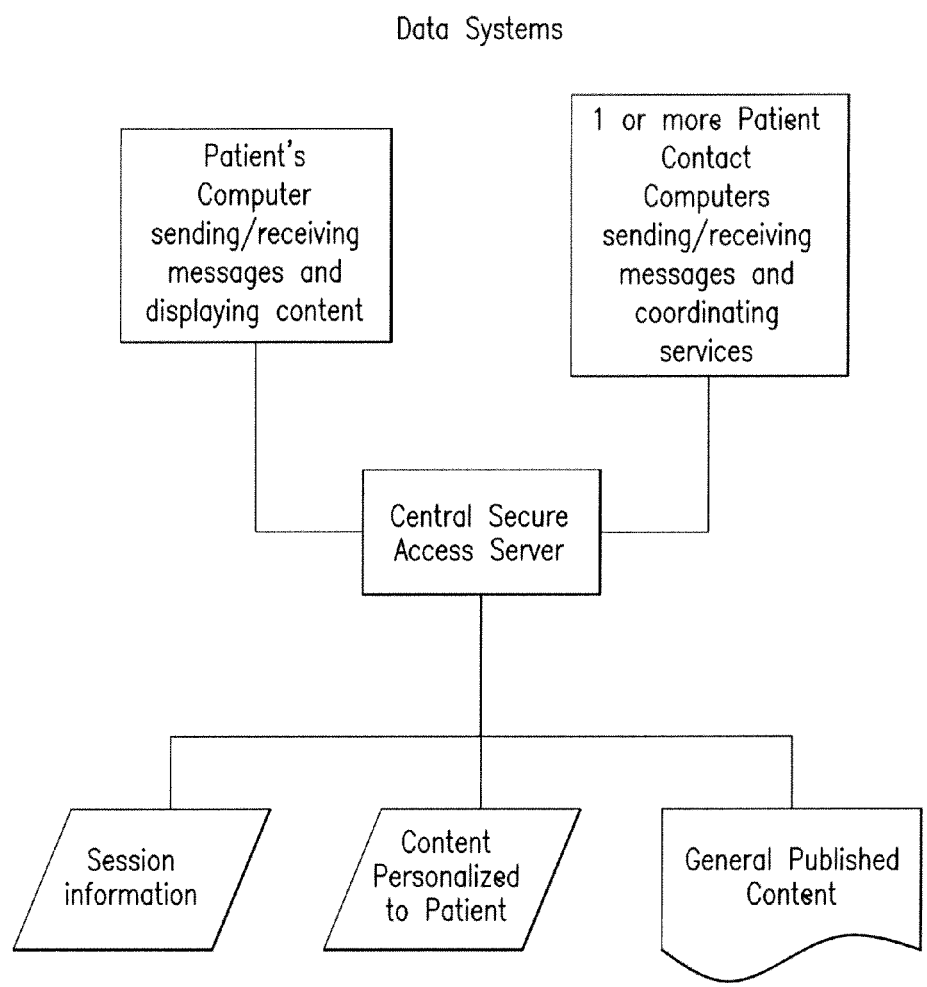
FIG. 17 is a flow diagram illustrating an exemplary flow of information and data.

As seen in FIG. 14, by clicking or activating an alert, the full text of an alert message is provided to the user. The text or multimedia including audio, video or other methods is customized and tailored (as discussed supra) to a specific user or to a class of users to be more likely to motivate a change or to get the user's attention. As is seen in FIG. 15, the expert advice could come by way of alert, or reminders, or events contained in the consumer's calendar.

The Healthspace efficiency index is effectuated by providing a scoring method of categorization and metrics, calculating bench marks, and by providing a change agent. The scoring method by categorization and metrics includes defining categories as collection of metrics or key performance indicators (KPIs). Categories include any or all areas of healthcare benefits including claims, utilization, risk profiles, predictive modeling, care management intervention, statistical models, evidence based medicine, or any healthcare related category that could be objectively measured.

Comparative risk profiles, medical or pharmacy claims, adherence to evidence based medicine, health or pharmacy benefit utilization all provide factors towards the scoring of the efficiency index. As the system is an inclusive healthcare management system bringing together service providers with consumers, a wealth of information is available in the aggregate for analysis and statistical processing to arrive at efficiency indices. FIG. 22 shows an exemplary predictive model utilizing Johns Hopkins Adjusted Clinical Groups (ACG) software to forecast risk and financial information as well as classify patients into different condition categories based on healthcare claims information.

Metrics or KPIs are measures of healthcare utilization or behavior unitized into numeric values, scores, or points. Illustratively, in a category of pharmacy benefits, a metric could be that a patient is utilizing a multi-source brand-name drug. This metric could potentially have 60 points assigned to it. Because this multi-source brand-drug has a generic equivalent, the patient might only receive 30 points for compliance and 0 points for failing to use a generic equivalent. In this example the metric could be combined or separated into individual components. In other words, the consumer could be provided with some points for following a doctor's advice, but even more points, for using a generic drug when one is available, and fewer points for using a brand-named drug when a generic is available. In aggregate, by the accumulation of these points, a user's efficiency index reflects the aggregate of the user's efficient utilization of certain categories of their healthcare benefits. Thereby, consumers' choices are capable of being monitored and incentivized or penalized towards a more efficient utilization of the healthcare coverage.

The numeric value, score, or points in the metrics or KPIs are weighted statistically or modeled statistically to improve the performance of the efficiency index.

In the calculation of benchmarks, every individual may be scored individually so that a total efficiency index, preferably a percentage, or score may be given to that individual. The individual score is then compared to the individual's peer groups' score or the scores of individuals of the same group. For example, an individual may be an employee and a peer group may be the average score of all the other employees of the same employer group. Alternatively an individual may be compared to everyone in their same age bracket and sex band.

A peer group may be scored and compared to other peer groups. For example one employer group achieving 80% efficiency rating may be compared to another employer group achieving 50% efficiency rating. The formula or calculation of the total score may be calculated by the total points achieved divided by the total achievable points for an individual. This score may be weighted and/or changed using other statistical models for other calculations, for example: forecasting costs if efficiency is improved.

With the aggregation and interconnection of records and service providers and consumer information, comes the ability to statistically measure and arrive at efficiency indices. By providing inefficient users of the healthcare benefits package or healthcare management system with a relatively lower score and by providing suggestions and incentives, it is seen that the consumer is empowered and motivated to raise their efficiency index. In doing so, they raise their efficient use of the healthcare benefits and the healthcare management system and lead a more beneficial, healthy life, while at the same time, save money for the insurers, caregivers and other service providers. Thereby, the cost of insurance and of providing care is reduced. This reduction in costs would not only pass on to the shareholders of those institutions, and to caregivers, or service providers, but ultimately passed back to the consumers themselves.

To effectuate this change, a change agent is provided. Through the combination and consideration of both scoring method and benchmarking, the healthcare efficiency index change agent gives corrective action suggestions (which may be customized or tailored to the individual consumer to be most effective) and/or recommendations to improve the overall efficiency of consumers. This may be applied to caregivers or service providers to help them become more efficient. To facilitate this, consumers are given individualized scores for categories and metrics and also given corrective action suggestions or recommendations to change or improve their respective scores. As soon as the system receives the updated information the scores are automatically updated.

Incentives may be used to help promote and change behavior of the patient towards more efficient use of healthcare. For example, some incentives may include zero co-pay for using a generic prescription, or lower deductibles and better rates for utilizing one method of the benefit plan over another. Indeed, any suitable incentives may be used.

Figure 18:
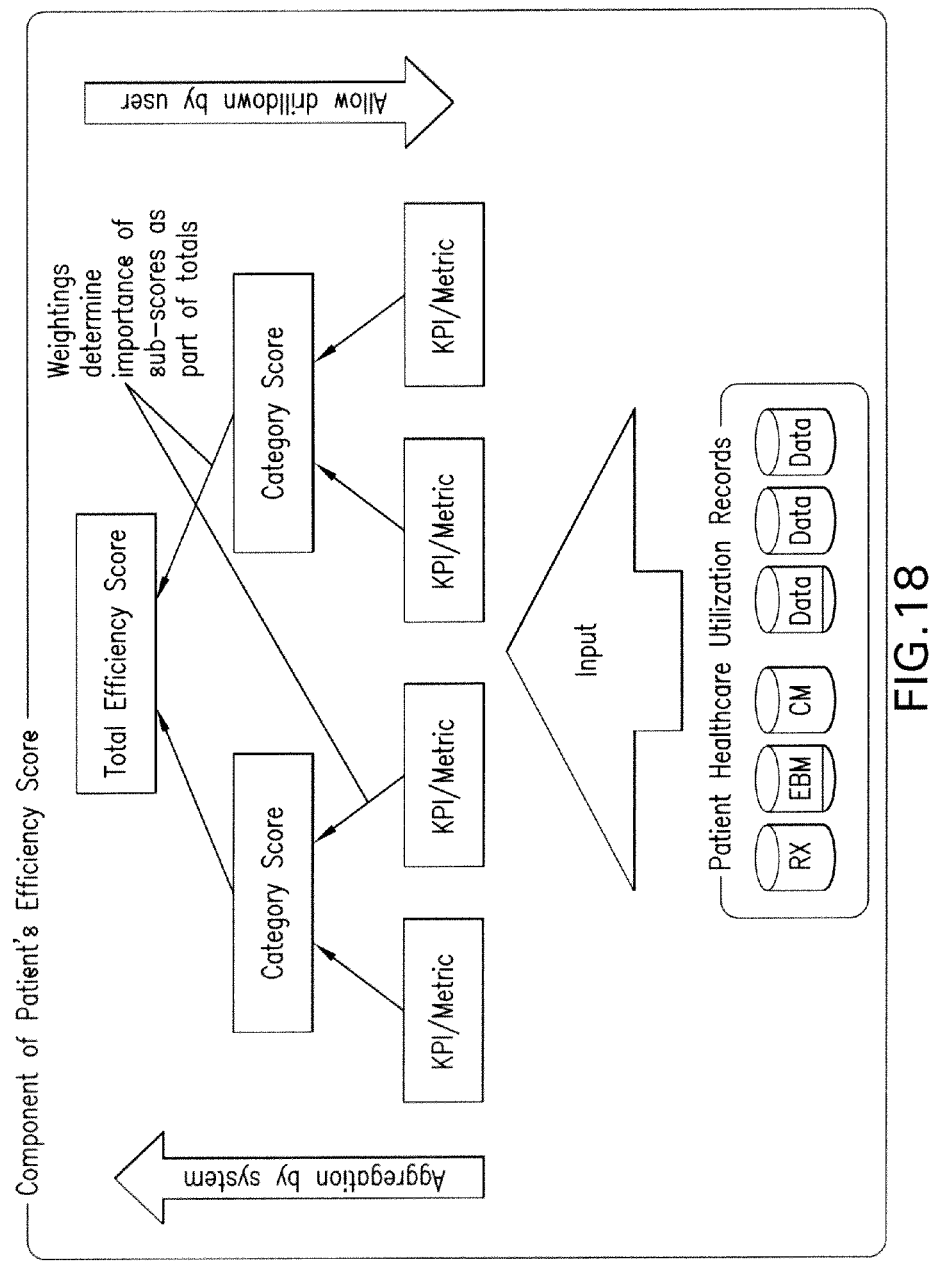
FIG. 18 is a diagram schematically illustrating components of a patient's efficiency score.
Figure 19:
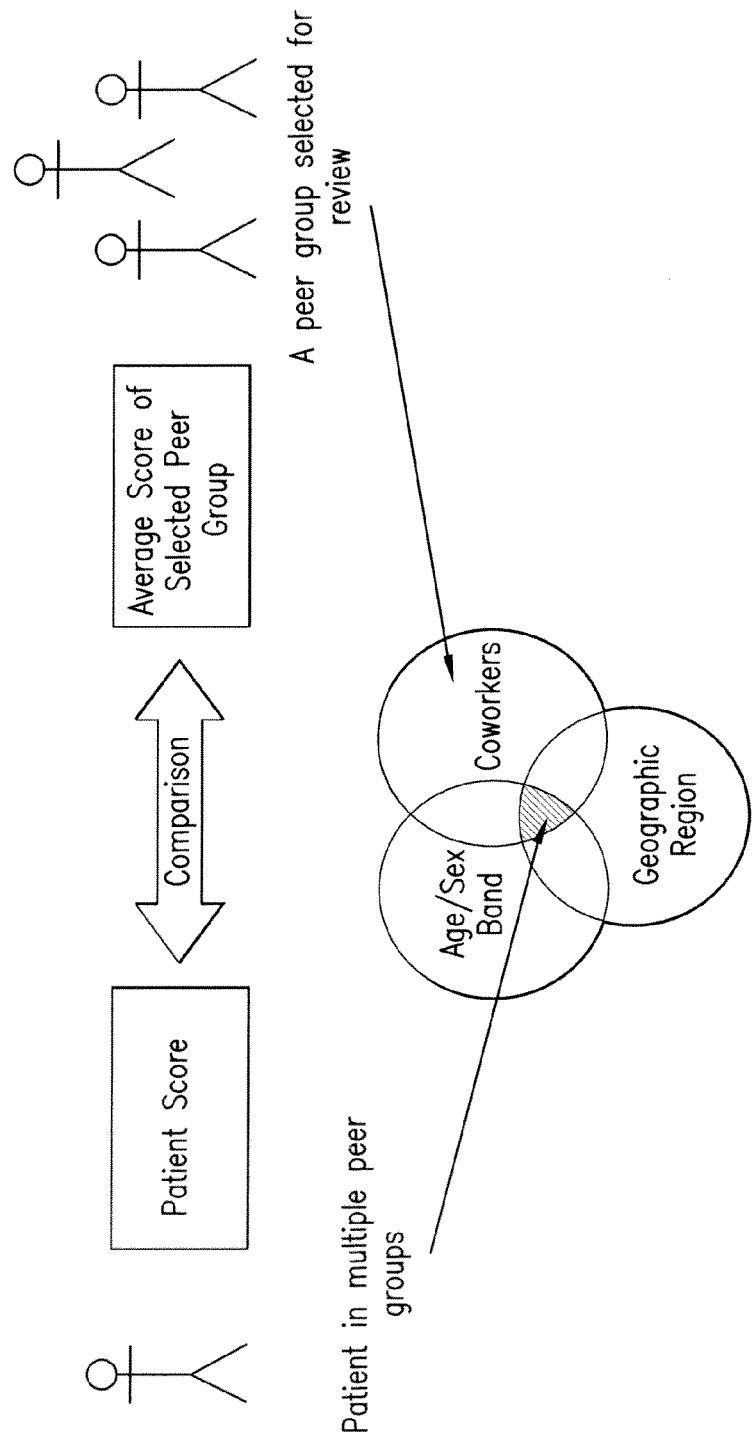
FIG. 19 is a chart illustrating comparisons of efficiency scores.
Figure 20:
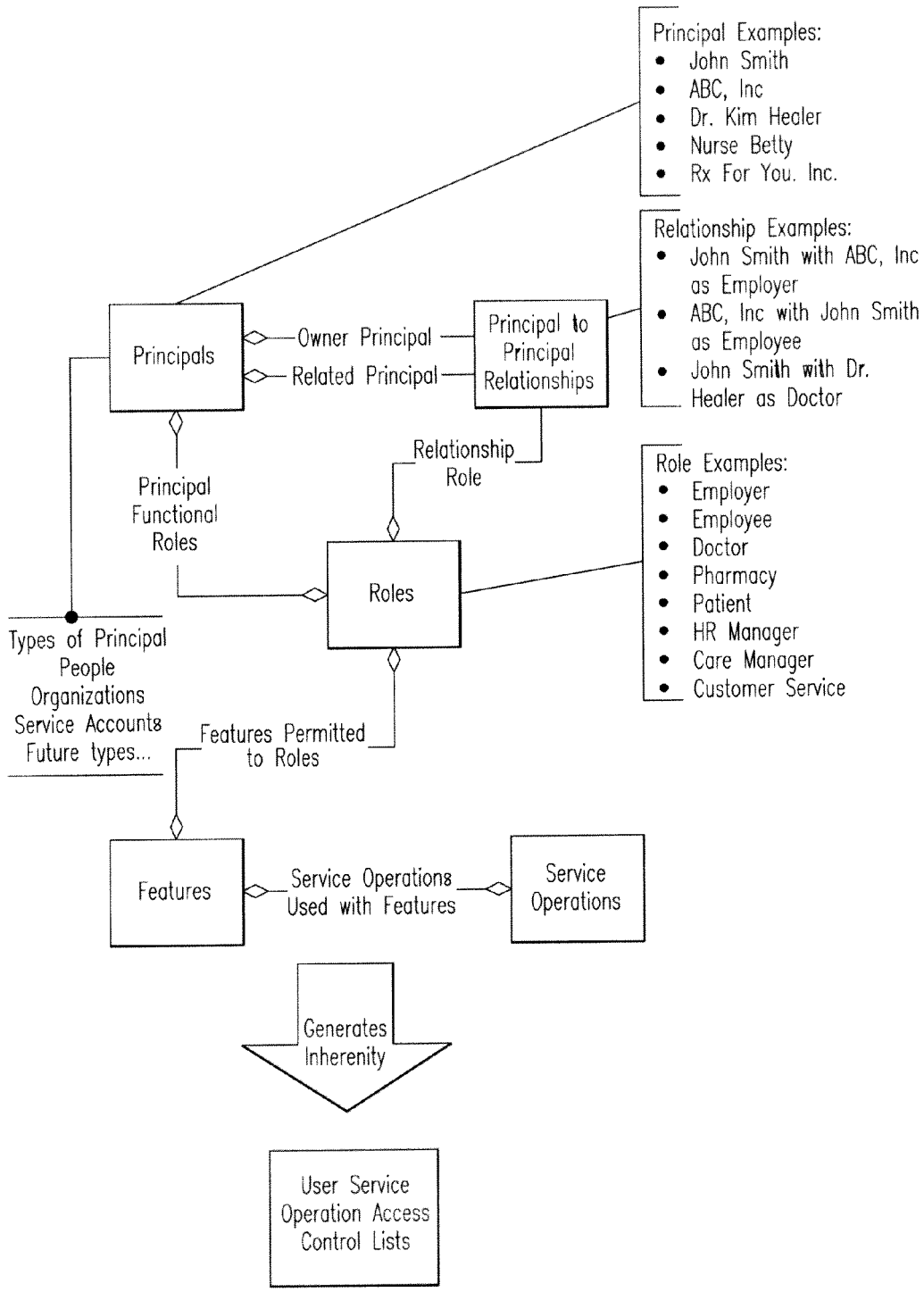
FIG. 20 is a chart illustrating principals, relationships and roles.

It can be seen in FIG. 18 that the patient healthcare utilization records of prescription, claims and assorted data are harvested as input into the total efficiency score calculation by decomposing into category scores and assigning weights to each category. By using KPIs and metrics to aggregate data on an individual consumer, suggestions may be correspondingly made. As seen in FIG. 18, a consumer or user, or even a service provider, may be allowed to view the calculation method, factors, or the relative weight of each category to have more bearing on the overall efficiency score and thereby selectively choose fields in which to improve or follow suggestions by which to receive incentives. FIG. 19 illustrates a patient score being compared with an average score of a selected peer group.

While some consumers will be hesitant, apathetic, or resistant to following suggestions to improve their efficiency index, the healthcare management system, through various techniques, such as surveys or risk assessments or questionnaires, is able to segment users into different segments, different segments of users tending to respond similarly to certain stimuli. Each segment may then be strategically targeted with narrowly tailored messages or stimuli.

For example, the universe of consumers may be segmented into different segments based upon behavioral, psychographic, demographic, or other data through the use of questionnaires or typing tools or any other methods to more effectively target that segment of the population. For example, it can be seen that potentially one segment of users may respond well to a short message explaining the effects of a preferred approach whereas another segment may prefer to see (and be more likely to respond to) empirical evidence, research, and actual case studies. Thereby customized messages may be sent to different segments of the population to encourage them to follow suggestions of an efficiency index program to increase their efficient utilization of the healthcare management system or the benefits package to which they subscribe.

Click Operations or ClickOps are another methodology for effectively reaching a low efficiency user to assist them to improve their efficiency. ClickOps is able to provide a means to track the actions that users perform in the system. These actions can be analyzed to search for desirable patterns of action that may lead to, or be correlated with, a high user efficiency.

Users monitored by ClickOps could be any user or provider of healthcare. ClickOps may be implemented by having the system track all actions by recording a "clickpoint" which is a log of a user interaction, or transaction, or transaction that relates to a user. Health plan activities, actions, and user activities or actions are independent clickpoints. An illustrative list of potential clickpoints include: any user action in the system, any user access of the system, claims data, a related clinical protocol, an assignment/capture of evidence based medicine data, a trigger or alert, an appointment, financial information, or other healthcare-related data point. "Clickstreams" would then include a series of individual clickpoints, including dates and times of the users while they are online on the healthcare management system. This allows the system to capture and analyze user behavior and component use within the Healthspace in aggregate.

By way of example, focus may be placed on the users who have an increasing efficiency index or are at a high efficiency index. By studying the actions of users with an increasing efficiency index, a template or suggested pattern or course of conduct may be suitably formulated through the aggregate study of such users and their clickstreams. This model of corrective action may then be suggested through the messaging efficiency tools described herein to effectively convey to different segments of consumers recommended methods for raising their efficiency index. Not only are individual users able to be provided with suggestions to increase their efficiency index, but also Click Operations allows the capture and analysis of care protocols and clinical guidelines.

Information derived from click stream analysis of both employees/patients and healthcare professionals gives feedback on health efficiency in several important areas, including: user health, healthcare professional performance, plan performance, and Healthspace performance. In previous systems, this type of data, if it even exists, is qualitative at best, and the lack of solid information is one source of financial waste in healthcare.

Clickstreams may reveal what components of a healthcare social network, platform, or system, such as Healthspace, are being accessed, the frequency of access, the order of access (i.e. is there a typical flow?), and which healthcare professionals/service areas are using Healthspace. Conversely, clickstreams may also reveal which components are rarely or never used.

The efficiency or effectiveness of a clinical pathway within Healthspace is able to be analyzed and suggestions or conclusions may be observed from the aggregation of different users' pathways. The click stream and pathway of the efficiency index is able to be analyzed. Administrators are enabled to analyze the click stream and pathway of care protocols and clinical guidelines to make judgments on effectiveness. The ultimate impact of a particular clinical pathway or user behavior as related to financial impact is able to be evaluated. Click Operations analysis may also be fed into a pay for performance system, allowing metrics and analysis of healthcare provider services.

Taken further, statistical analysis of clickstream data, in aggregate, may inform or identify: the best, or most widely used services, features, functions, and products of Healthspace; which features, functions, products are frequently combined; Return On Investment (ROI) based upon usage data of elements or combinations of elements within Healthspace; elements of Healthspace that should continue to be offered versus those that should be dropped. Usage that results in modified (i.e. more healthful) behavior among users and usage that results in higher plan efficiency (e.g. what services, features, functions, and products encourage users to switch to generic drugs, or become more compliant with treatment plans) may be ascertained. The user behaviors that affect users' claims history, and ultimately, financial impact on the plan are able to be analyzed. The efficacy of health plan programs, services, features, functions, and products in increasing efficiencies and ultimate cost savings are able to be analyzed through the ClickOps. Still further, ClickOps facilitates analysis of user financial incentives for increasing efficiency index through health-related behavioral improvements (e.g. weight loss, smoking cessation, etc.).

Not only are consumers'/clients'/patients' clickstreams able to be analyzed to improve the efficiency of the system, but also healthcare professionals' clickstreams are able to be analyzed to provide insight, and ultimate improve the system as well. The ClickOps system is useful in identifying best practices from comparisons between actual medical protocols versus those provided by an "expert system" such as the VA Health System. In other words, comparisons are able to be made between actual clinical protocols versus the accepted "best practice" protocols. This may provide insight on extraneous health spending, reduce unnecessary tests or procedures, and identify gaps in care. A similar comparison is able to be made against evidence based medicine protocols. The financial impact of a clinical pathway and resulting claims history on a plan are able to be assessed.

Best practices are able to be identified by analysis of claims processing and financial results click streams. For example: which alerts and health-related interventions result in modified patient/physician cost-containment behavior. Moreover, given certain plan or healthcare professional interventions, the percent efficiency or cost savings of a behavioral change is able to be ascertained. As a specific example: if a physician writes a patient a prescription for a drug, for which there is an equivalent generic, an email alert may be automatically sent to the patient advising them that an equivalent, but less expensive, generic medicine is available. This may result in a calculable and perhaps statistically significant increase in the percentage of prescriptions filled with a generic versus those filled with a generic by patients not sent an alert. It may also be found that if a case manager follows-up with a phone call after the alert to personally explain and assist the patient (who has not yet done so) in switching to a generic medication results in a larger, and statistically significant, percentage of patients who use a generic. A plan or employer may find that the additional cost of such proactive educational measures is an effective way of containing cost and increasing healthcare efficiencies.

Support for Pay-for-Performance systems are also incorporated. Production of data based upon click points or click streams that enables quantitative tracking of healthcare successes enables performance-based pay to healthcare professionals for the services they provide. For example, smoking continues to be a high-risk behavior, yet traditional health reimbursement plans often do not compensate physicians for advising and assisting patients to quit. A physician who consistently provides smoking cessation services and communications to patients, resulting in successful quit attempts is able to be tracked with ClickOps and the physician may be compensated according to his/her efforts and outcomes.

Figure 26:
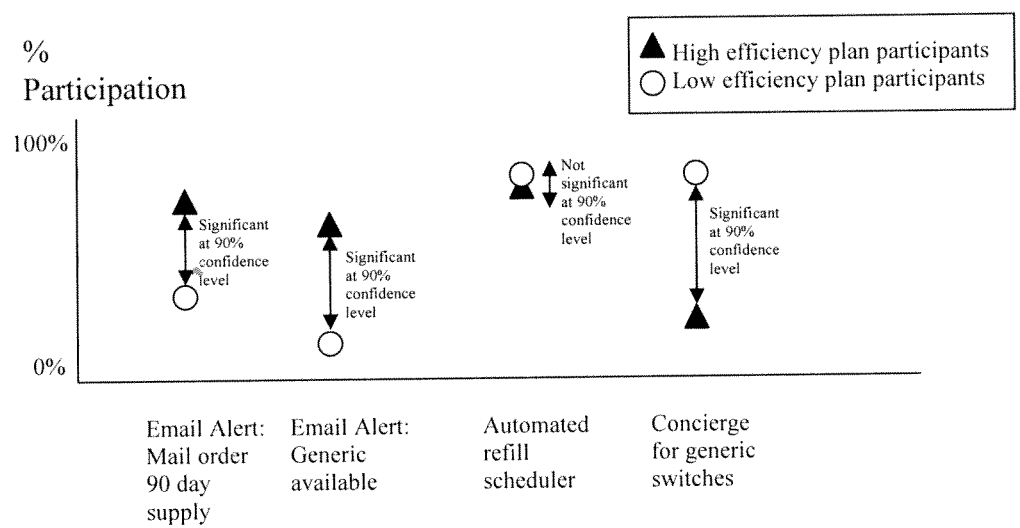
FIG. 26 is an illustrative example of a click stream of the present invention.

FIG. 26 shows an example of a clickstream; the clickstream includes four distinct click points. The vertical axis on the clickstream represents percent participation for each click point. A series of click points are identified along the horizontal axis, comprising the clickstream. The exemplary clickstream represents data from a subset of health plan participants who use one or more maintenance prescription medications. These participants have been prescribed a medication to be used for longer than 90 days. The four click points in the example are: (1) email alert that 90-day supplies of medication are available for a lower cost via mail-order; (2) email alert that a generic equivalent medication is available; (3) usage of an automated refill scheduler that provides refills via phone or email authorization; (4) concierge service that coordinates generic switches with physicians.

Statistical analysis of the clickstream shown in FIG. 26 reveals that email alerts regarding 90-day mail-order supplies and available generics are sent to a statistically significant number of high efficiency plan participants as opposed to low efficiency plan participants. The recommendation to the plan is to require all participants to receive such alerts to drive efficiency.

It may also be seen in the example clickstream that no significant difference in the usage of an automated refill scheduler is seen between the high and low efficiency plan participants. However, a large proportion of participants use this service. The recommendation to the plan may be to continue to offer the service because it is widely used by participants and not costly.

Still further, from analysis of the exemplary clickstream of FIG. 26, it can be seen that low efficiency plan participants are significantly more likely to use the concierge service for getting physician authorization to generic switches, whereas the high efficiency users are not. This service does not correlate with increased efficiencies. The recommendation to the plan may be to discontinue this service as it is costly and requires personal intervention, while not providing an increase in efficiency. A plan administrator may instead focus resources on helping the low efficiency plan participants to get their maintenance medications via mail-order and alert them about switching to generics.

Figure 27:
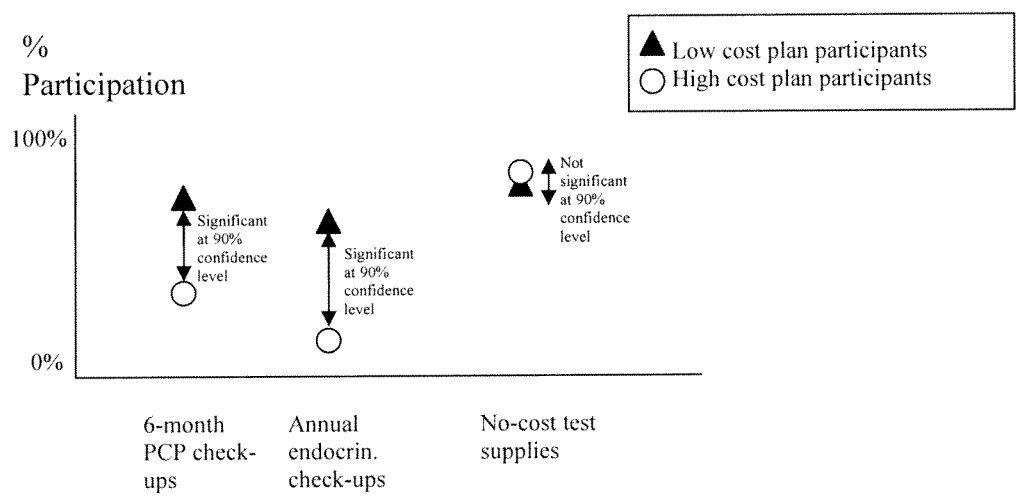
FIG. 27 is an illustrative example of another click stream of the present invention.

FIG. 27 shows another example of a clickstream leading to different interpretations. The clickstream relates to treatment and care of a group of patients with diabetes. The click points represent: (1) 6 month primary care physician (PCP) check-ups, (2) annual endocrinologist visits, and (3) no-cost blood sugar testing supplies.

Statistical analysis and interpretation of this click stream reveals that plan participants with diabetes who are high cost patients do not regularly have 6-month PCP check-ups or annual endocrinologist check-ups. High cost could equivalently be related to higher numbers of inpatient days per year (as revealed from claims data), higher risk scores when assigning plan cost to these patients, and more. Clickstream analysis therefore enables employers, health plans administrators, patients, and healthcare providers to effectively assess cost, risk, efficiency, compliance, or any other type of metric that may be measured.

An underlying part to such analysis of a clickstream is identifying who is a high efficiency plan participant and, conversely, who is a low efficiency participant. FIG. 27 illustrates patient participants, but also, healthcare professionals could be classified as high and low efficiency users of a healthcare social network or system.

A variety of methodologies may be used to rank efficiencies, costs, or risks of users, including: hard thresholds (e.g., at or above 50% efficiency is a high efficiency user, whereas, below 50% efficiency is a low efficiency user); thresholds based upon the number of standard deviations from the mean of a given population (e.g., low efficiency users have efficiencies on standard deviation below the mean efficiency, moderate efficiency users have efficiencies within one standard deviation of the meant, etc. . . . ).

The statistical methodologies of ClickOps analysis may include: Confidence intervals, Z-tests, T-tests, chi-square tests, or other methods for determining differences between groups. Here, results obtained from independent groups may be compared, and it may be determined whether the groups are significantly different, based upon a particular confidence level.

1. A T-test may be used to compare a sample mean to a population mean:
   a. $t=(x_{bar}-\mu_0)/(s/sqrt(n))$, where $x_{bar}$ is the mean of the sample, $\mu_o$ is the mean to which the sample mean is being compared, s is the standard deviation of the sample, and n is the sample size. For a given t-value and confidence level, statistical significance may be measured.

2. A Z-test may be used to compare two independent samples, with a population in which the standard deviation is known for a given value
   a. $z=(x-\mu)/(\sigma/sqrt(n))$, where x is the score to be standardized (compared), $\mu$ is the mean of the population, $\sigma$ is the standard deviation of the population, and n is the sample size. Again, for a given z-value and confidence level, statistical significance of a value is able be determined.
   b. $z=(phat_1-phat_2)/sqrt[phat\times(1-phat)(1/n_1+1/n_2)]$, where $phat_1$ is the sample proportion of group 1 ($x_1/n_1$), $phat_2$ is the sample proportion of group 2 ($x_2/n_2$), phat is the weighted average of $phat_1$ and $phat_2$ $[(x_1+x_2)/(n_1+n_2)]$, $x_1$ and $x_2$ are the observed values, and $n_1$ and $n_2$ are the two sample sizes. After calculating this z-statistic, one is able to determine whether the two observed values are significantly different given a certain confidence level.

Another functionality provided by the healthcare management system of the subject Patent Application is a way for users to bookmark items of interest allowing them to easily recall and find items or objects that are particularly relevant or will be needed in the future. These items or objects of interest may include websites, contacts, informational resources, alerts, reminders, suggestions on increasing efficiency index. These bookmarks are then available for sharing with other consumers or service providers. This allows for the verification by service providers of the accuracy, or the applicability, of a bookmarked item to a particular consumer.

While the healthcare management system seeks to interface caregivers or service providers and consumers or users, and also make readily available resources such as information and contacts and suggestions, another feature is to restrict some information and some resources to be more context sensitive. For example, when the user searches for doctors, rather than providing the user with the entire universe of doctors, a context sensitive list may be provided. For example, when a consumer searches for a list of doctors, preferentially doctors that are in-network could be provided first or even at the exclusion of out-of-network service providers. By providing these in-network doctors or service providers first or exclusively, a user or consumer is quickly able to find an in-network solution that will save them money and will also potentially save the insurance provider money as well. This allows the removal of much uncertainty in the process of selecting a caregiver. Were one simply to conduct an open search for doctors, there is a high probability that a user or consumer ends up with a doctor that is out-of-network and thereby incurs potentially great and unexpected costs. With the aggregation of vast amounts of information, the system is able to be context and location aware.

For example, generally a user searching for a doctor might want a doctor to be proximate to either their home address or their work address or another address that they frequent. This may be accommodated quite easily as the system already knows the consumer's home address, work address, or any other address that the user has input into the system. As a matter of convenience, the system may also provide service provider ratings and reviews or other research, such as a service provider's efficiency index.

As it provides a trusted portal, the healthcare management system also provides look-up information on drugs such as interactions, contraindications, or side-effects, thus allowing the user to avoid or catch potential interactions, side-effects or problems that could arise, in advance. A user/consumer may even be provided with information relating to gaps in care using evidence based medicine or other approaches. Indeed, a broad variety of self-serve healthcare research tools are provided that will improve the health of the consumer. For example, a medicine cabinet feature is provided that lists the consumer's current drug regimen/claims and offers potential equivalent therapeutic alternatives, perhaps at lower costs. It is important to note that each such feature would need prominent disclaimers to inform the consumer that only their doctor may change their prescription. Nonetheless, a potential equivalent therapeutic alternative of interest to a consumer may be bookmarked and shared with that consumer's doctor for their input or consideration.

Each consumer or service provider is provided with a profile. Each profile has various management tasks associated with it that a consumer or service provider would be authorized to change, pursuant to their security authorizations based on relationships of trust or their user name and password. A personal profile preferably describes basics related to healthcare services including demographics, insurance plan reference, dependents list or other such characteristics of a consumer or service provider. In this section the user may manage the application settings or the client software program settings on their platform.

The healthcare management system of the subject Patent Application provides for a developer network or an application programming interface (API). This developer network API allows external service providers a standard platform to access and extend the applications. By allowing external service providers such as insurance companies, physicians, hospitals, and pharmacies to extend the applications and services and access data this, the utility of the platform to the service providers is enhanced by making it easy for them to integrate with and connect with not only their current consumers but also a large numbers of potential consumers. This saves the external service providers time and money by obviating the need to create their own application to interact with consumers and potential consumers. This in turn allows for easier adoption of their services.

However, in allowing the extension of applications there is an increased potential for compromise of security. To counteract that threat, a multi-level certification process to ensure patient security and privacy is enacted whereby only trusted external service providers are able to extend applications. As a further precaution, each application or extension provided by each external service provider is subjected to review and certification by the administration of the healthcare management system or independent auditors.

To facilitate the ease of use by consumers, the client software program for each platform is preferably delivered through the web, being distributed and executed in a trusted host or "sandbox" environment. To allow for the greatest universe of potential users, a simple access-and-use methodology is adopted. Keeping the interface simple and intuitive in this manner enables all users including the elderly or children or the handicapped to more conveniently access and self serve.

Automatic version updates are feasible with limited or no elevation of host access rights or user intervention. In other words, the upgrading process is relatively automatic in that, by using the web for application delivery, the user is able to simply authorize the upgrade and the system is able to do the upgrading automatically. For example, this may be accomplished through a browser-based application or "click once" deployment.

Clients access the application data preferably through the web services which are designed to allow access of client programs from multiple platforms. The services don't need to be rewritten for each independent platform but instead are abstracted, and only the client program is written for each individual platform. The services will access a centralized server or server farm that is a portal to data. However, it is important that the database back-end be isolated from direct public access and provisions are made that databases are only accessible through services called through certified client programs. User's machines have a trusted client program installed and the back-end database is secure. To ensure that the paths therebetween are reliable and private, secure channels are established between the client and the server which are both encrypted and username/password protected.

Figure 23:
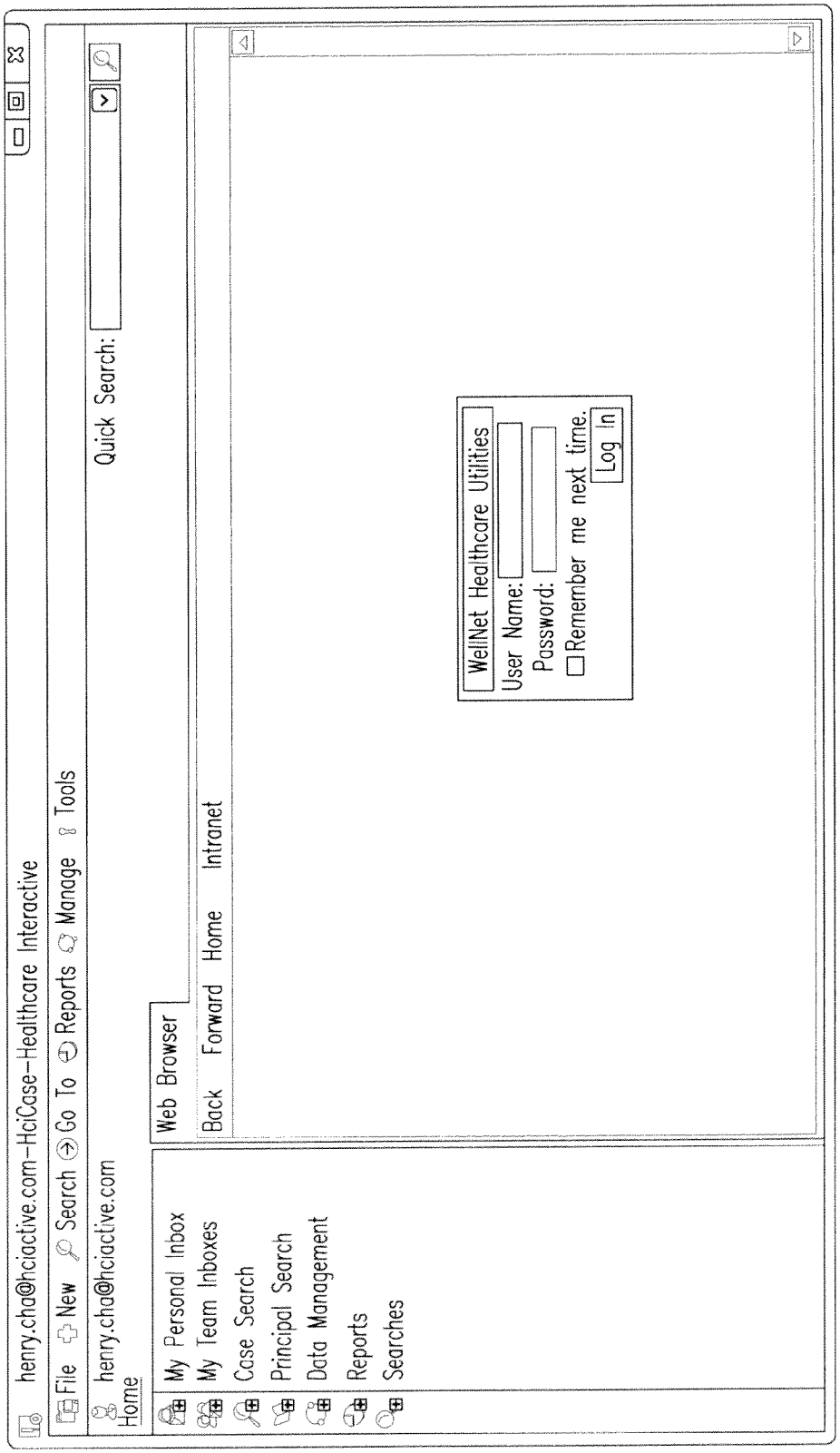
FIG. 23 is an illustrative example of a display of a graphical user interface of a third application of an exemplary embodiment of the present invention.
Figure 25:
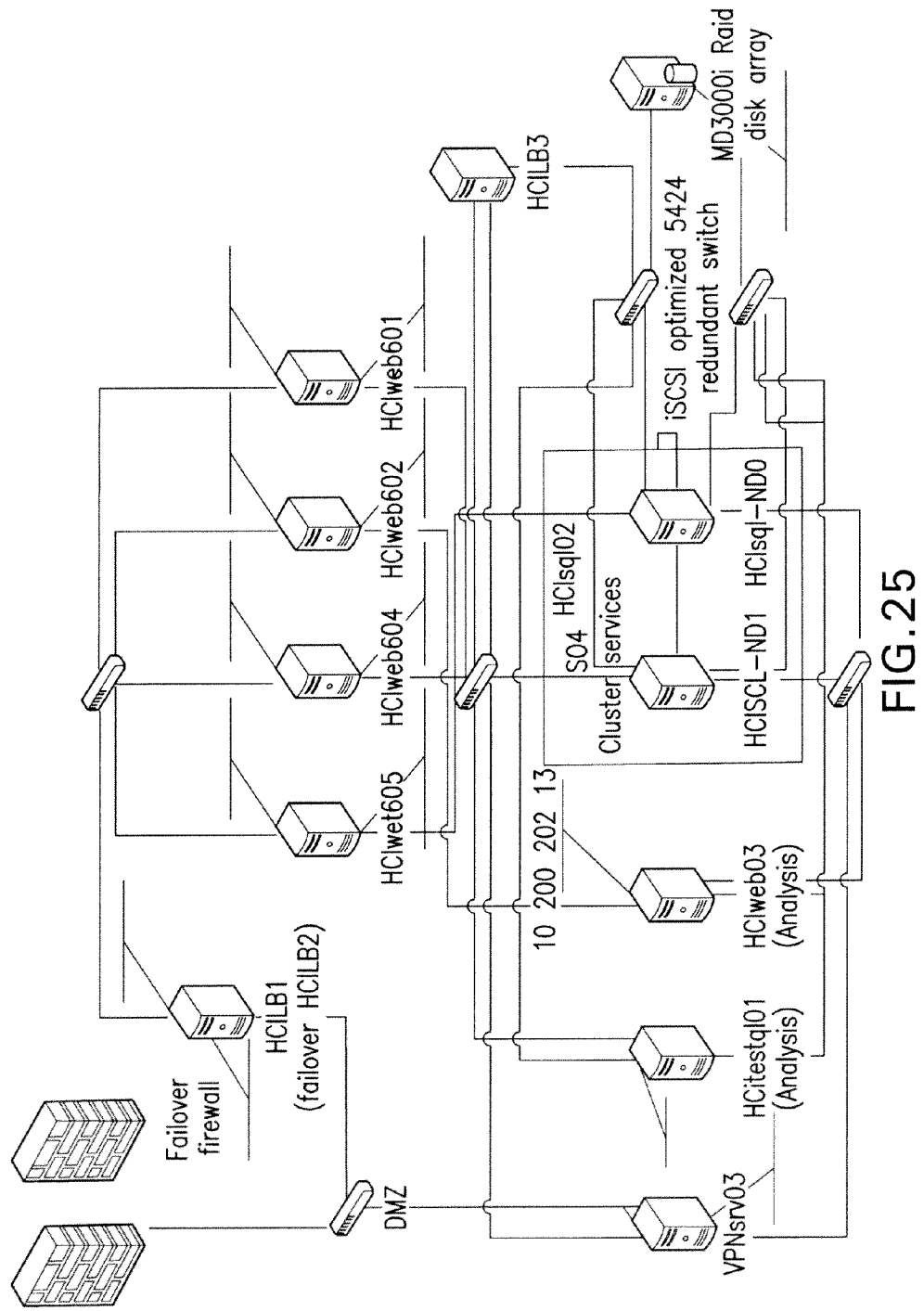
FIG. 25 is a schematic block diagram illustrating an exemplary arrangement of nodes of a system architecture within a portion of a hierarchical tree defined in accordance with the present invention.

Another benefit flowing from this abstraction and separation of the back-end is that the back-end database portion is able to integrate with other standard healthcare applications including account management, claims management, predictive modeling, health risk assessment, care management, and the like. To facilitate this, the system employs industry standard data warehousing techniques to store data in de-normalized multidimensional structures that allow for efficient performance for analysis and reporting. FIG. 23 illustrates another exemplary client program built on the Healthspace platform.

Figure 24:
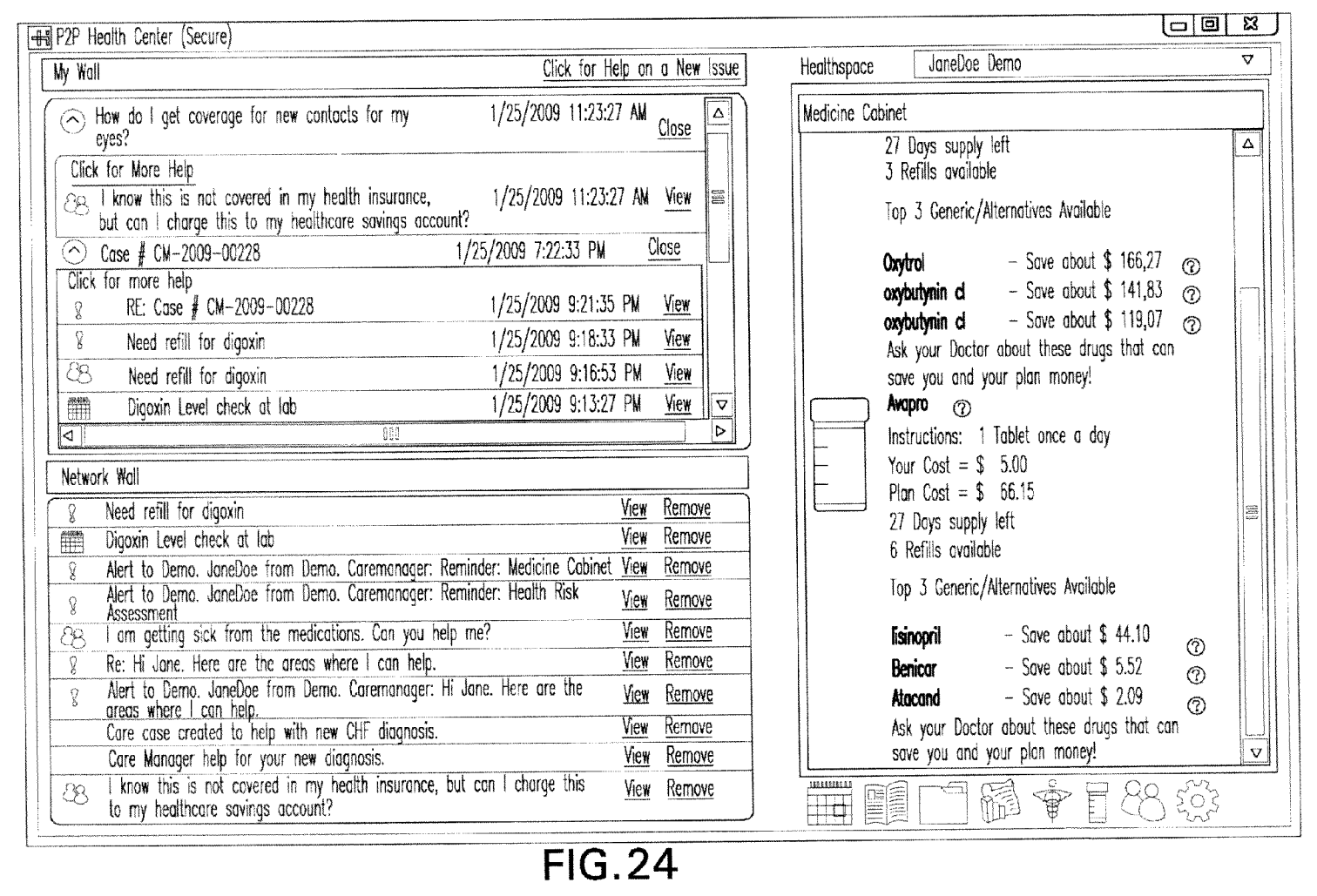

These functionalities are able to be extended through the use of strategic partnerships and the integration of other external service providers allowing external developers to extend the client interface with additional services or integrate with additional back-end systems or create clients on additional platforms. For example, as seen in FIG. 24, the "Medicine Cabinet" tab utilizes Destination RX's web service as a virtual database. The Healthspace platform sends a query to the Destination RX web service and receives back information such as: days left of prescription, refills available, generic alternatives, instructions, costs, and cost savings.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular combinations of flows or processing steps may be reversed or interposed, all without departing from the spirit or scope of the invention as defined in the appended Claims.

What is claimed is:

1. A network based healthcare management system utilized for functional interaction by a plurality of principals, the system comprising:
    a plurality of client devices;
    a host server;
    a network coupling said host server with said plurality of client devices;
    a plurality of user profiles stored on said host server, said plurality of user profiles each defining privilege parameters based on a combination of user role and identity;
    a plurality of service operation modules stored on said host server each selectively set with a corresponding relationships requirement between interacting principals;
    a plurality of different client applications, at least one stored on each client device, each client application being compatible for coupling with at least one service operation, wherein access to each of said service operations is selectively restricted responsive to an access determination based on a combination of client application identity and said privilege parameters, the access determination being made in adaptive manner based on a session context monitored by said host server and compliance with the relationship requirement corresponding to the service operation;
    wherein said service operations control access by generating an access denied exception if the client application is unregistered with the service operation, said privilege parameters for each user profile are stored in an access control list (ACL).

2. The network based healthcare management system as in claim 1, wherein each client application is written in eXtensible Application Markup Language (XAML).

3. The network based healthcare management system as in claim 1, wherein each client application communicates with said host server through eXtensible Markup Language (XML).

4. A method of restricting access to service operations of a healthcare management system utilized for functional interaction by a plurality of principals, comprising:
   (a) establishing a plurality of pre-stored user profiles within a network;
   (b) defining a plurality of privilege parameters for each user profile based on a combination of user role and identity;
   (c) establishing a plurality of different client applications for accessing a healthcare management system within said network;
   (d) establishing a plurality of service operations within said network for performing functions for said client applications, the service operations each selectively set with a corresponding relationships requirement between interacting principals;
   (e) registering each client application with at least one service operation;
   (f) displaying at least one preselected client application feature to a user profile;
   (g) actuating at least one of the displayed client application features responsive to a user's selection;
   (h) determining if said actuated client application feature is registered with a service operation correlated with said actuated client application feature;
   (i) generating an access control signal according to an access determination based on a combination of registration state of said actuated client application feature with respect to said correlated service operation and said privilege parameters, the access determination being made in adaptive manner based on a session context monitored by said host server and compliance with the relationship requirement corresponding to the service operation;
   wherein said generating an access control signal includes generating an access denied exception if the client application is unregistered with the service operation, and said plurality of privilege parameters for each user profile are stored in an access control list (ACL).

5. The method of restricting access to service operations of a healthcare management system as in claim 4, wherein each client application is written in eXtensible Application Markup Language (XAML).

6. The method of restricting access to service operations of a healthcare management system as in claim 4, wherein each client application accesses a healthcare management system within said network through eXtensible Markup Language (XML).

7. The method of restricting access to service operations of a healthcare management system as in claim 4, further comprising automatically generating and diagnostically reporting to users a strategy for optimizing use of the healthcare management system, wherein:
   (a) a plurality of user profiles with healthcare utilization parameters within a network are established;
   (b) a transactional history for each of said user profiles is compiled according to said healthcare utilization parameters;
   (c) the transactional history of each user is comparatively evaluated relative to a predetermined criteria tied to the transactional history;
   (b) said users are classified according to the comparative evaluation of each user into an ideal group and a non-ideal group;
   (d) said transactions of at least one user belonging to said ideal group are analyzed to identify remedial steps for users of said non-ideal group;
   (e) said remedial steps are prescribed to a non-ideal user for implementation to become an ideal user.

8. The method of restricting access to service operations of a healthcare management system as in claim 7, wherein said ideal group includes efficient users.

9. The method of restricting access to service operations of a healthcare management system as in claim 7, wherein said ideal group includes users with an increasing efficiency index.

10. The method of restricting access to service operations of a healthcare management system as in claim 7, wherein said non-ideal group includes inefficient users.

11. The method of restricting access to service operations of a healthcare management system as in claim 7, wherein said prescribing of remedial steps incorporates evidence based messaging.

12. A computer program product for restricting access to service operations of a healthcare management system utilized for functional interaction by a plurality of principals, the computer program product comprising a nontransitory computer readable medium comprising program instructions for:
   (a) accessing a plurality of pre-stored user profiles within a network;
   (b) defining a plurality of privilege parameters for each user profile based on a combination of user role and identity;
   (c) actuating a plurality of different client applications for accessing a healthcare management system within said network;
   (d) accessing a plurality of service operations within said network for performing functions for said client applications, the service operations each selectively set with a corresponding relationships requirement between interacting principals;
   (e) registering each client application with at least one service operation;
   (f) displaying at least one preselected client application feature to a user profile;
   (g) actuating at least one of the displayed client application features responsive to a user's selection;
   (h) determining if said actuated client application feature is registered with a service operation correlated with said actuated client application feature;
   (i) generating an access control signal according to an access determination based on a combination of registration state of said actuated client application feature with respect to said correlated service operation and said privilege parameters, the access determination being made in adaptive manner based on a session context monitored by said host server and compliance with the relationship requirement corresponding to the service operation;
   wherein said generating an access control signal includes generating an access denied exception if the client application is unregistered with the service operation, and said plurality of privilege parameters for each user profile are stored in an access control list (ACL).

13. The computer program product as recited in claim 12, wherein each client application is written in eXtensible Application Markup Language (XAML).

14. The computer program product as recited in claim 12, wherein each client application accesses a healthcare management system within said network through eXtensible Markup Language (XML).

\* \* \* \* \*